United States Patent
Tsubusaki et al.

(10) Patent No.: US 11,530,295 B2
(45) Date of Patent: *Dec. 20, 2022

(54) HYDROPHILIC POLYMER DERIVATIVE HAVING CYCLIC BENZYLIDENE ACETAL LINKER

(71) Applicant: NOF CORPORATION, Tokyo (JP)

(72) Inventors: Takuma Tsubusaki, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 131 days.

This patent is subject to a terminal disclaimer.

(21) Appl. No.: 16/887,081

(22) Filed: May 29, 2020

(65) Prior Publication Data

US 2020/0291178 A1    Sep. 17, 2020

Related U.S. Application Data

(63) Continuation of application No. 15/300,699, filed as application No. PCT/JP2015/060013 on Mar. 30, 2015, now abandoned.

(30) Foreign Application Priority Data

Mar. 31, 2014  (JP) ................... 2014-072356
Sep. 22, 2014  (JP) ................... 2014-193039

(51) Int. Cl.

| | |
|---|---|
| A61K 47/60 | (2017.01) |
| C08G 65/333 | (2006.01) |
| C07D 405/06 | (2006.01) |
| C08G 65/329 | (2006.01) |
| C07D 317/22 | (2006.01) |
| C07D 317/28 | (2006.01) |
| C08G 65/331 | (2006.01) |
| C08G 65/337 | (2006.01) |
| C08G 65/334 | (2006.01) |
| C07D 317/20 | (2006.01) |
| C07D 317/24 | (2006.01) |

(52) U.S. Cl.
CPC ..... *C08G 65/33396* (2013.01); *C07D 317/20* (2013.01); *C07D 317/22* (2013.01); *C07D 317/24* (2013.01); *C07D 317/28* (2013.01); *C07D 405/06* (2013.01); *C08G 65/329* (2013.01); *C08G 65/333* (2013.01); *C08G 65/337* (2013.01); *C08G 65/3317* (2013.01); *C08G 65/3346* (2013.01); *C08G 65/33324* (2013.01); *C08G 65/33337* (2013.01); *C08G 65/33341* (2013.01)

(58) Field of Classification Search
CPC ........... C08G 65/33396; C08G 65/329; C08G 65/3317; C08G 65/333; C08G 65/33324; C08G 65/33337; C08G 65/33341; C08G 65/3346; C08G 65/337; C07D 317/20; C07D 317/22; C07D 317/24; C07D 317/28; C07D 405/06

See application file for complete search history.

(56) References Cited

U.S. PATENT DOCUMENTS

| | | |
|---|---|---|
| 4,710,505 A | 12/1987 | Robin et al. |
| 6,548,126 B1 | 4/2003 | Sasada et al. |
| 2002/0013266 A1 | 1/2002 | Bentley et al. |
| 2002/0033472 A1 | 3/2002 | Kato et al. |
| 2006/0003326 A1 | 1/2006 | Lange et al. |
| 2013/0224870 A1 | 8/2013 | Vigh et al. |
| 2014/0039167 A1 | 2/2014 | McManus et al. |
| 2014/0051623 A1 | 2/2014 | Kratz et al. |
| 2014/0371133 A1 | 12/2014 | Francois et al. |

(Continued)

FOREIGN PATENT DOCUMENTS

| | | |
|---|---|---|
| GB | 1199110 A | 7/1970 |
| JP | 61-194084 A | 8/1986 |
| JP | 2001-139511 A | 5/2001 |

(Continued)

OTHER PUBLICATIONS

Communication dated Jan. 21, 2021 issued by China National Intellectual Property Administration in Chinese Application No. 201580018321.7.

(Continued)

*Primary Examiner* — Robert H Havlin
(74) *Attorney, Agent, or Firm* — Sughrue Mion, PLLC

(57) ABSTRACT

A hydrophilic polymer derivative having a cyclic benzylidene acetal linker represented by the following formula (1):

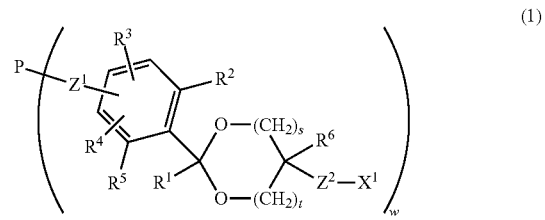

wherein $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $X^1$ is a chemically reactive functional group; P is a hydrophilic polymer; s is 1 or 2, t is 0 or 1, and s+t is 1 or 2; w is an integer of 1 to 8; and $Z^1$ and $Z^2$ are each independently a selected divalent spacer.

19 Claims, 2 Drawing Sheets

(56) References Cited

U.S. PATENT DOCUMENTS

| | | | |
|---|---|---|---|
| 2015/0073155 A1 | 3/2015 | Yoshioka et al. | |
| 2016/0326317 A1 | 11/2016 | Yoshioka et al. | |

FOREIGN PATENT DOCUMENTS

| | | | |
|---|---|---|---|
| JP | 2002-20344 | A | 1/2002 |
| JP | 2003-511357 | A | 3/2003 |
| JP | 2005-512978 | A | 5/2005 |
| WO | 2005/108463 | A2 | 11/2005 |
| WO | 2012/027717 | A2 | 3/2012 |
| WO | 2012/113571 | A1 | 8/2012 |
| WO | 2012/178083 | A1 | 12/2012 |
| WO | 2013/147015 | A1 | 10/2013 |

OTHER PUBLICATIONS

You Qidong et al., "Pharmaceutical Chemistry", National Planning Textbook in the Fifteenth-Year Plan of General Higher Education, Chemical Industry Press, 1st Edition, Jan. 2004, p. 33.

Communication dated Sep. 28, 2017, issued by the European Patent Office in European Application No. 15772451.9.

Communication dated Sep. 9, 2019 issued by the Japanese Patent Office in Japanese Application No. 2015-068326.

Communication dated Dec. 3, 2018 issued by the Japanese Patent Office in Japanese Patent Application No. 2015-068326.

Elizabeth R Gillies et al: "Stimuli-Responsive Supramolecular Assemblies of Linear-Dendritic Copolymers", Journal of the American Chemical Society, American Chemical Society, US, vol. 126, No. 38, Sep. 29, 2004 (Sep. 29, 2004), pp. 11936-11943, (8 pages total).

Gillies et al; "A new approach towards acid sensitive copolymer micelles for drug delivery"; Chemical Communication; 2003; No. 14; pp. 1640-1641.

Gillies et al; "Acetals as pH-Sensitive Linkages for Drug Delivery"; Bioconjugate Chem.; vol. 15; No. 6; 2004; pp. 1254-1263.

Hiki et al; "Design and Synthesis of Novek PEG Derivatives Integrated with Both PEGylation and DePEGylation Functionality"; 57th Annual Meeting of the Society of Polymer Science, Japan, Preprints of The Society of Polymer Science, Japan, 57, 1897; May 2008.

Huang et al; "pH-labile sheddable block copolymers by RAFY polymerization: Synthesis and potential use as siRNA conjugates"; European Polymer Journal; 2013; vol. 49; No. 10; pp. 2895-2905.

International Search Report dated Jun. 16, 2015 issued by the International Searching Authority in International Application No. PCT/JP2015/060013 (PCT/ISA/210).

Junqiang Zhao et al: "Acid-induced disassemblable nanoparticles based on cyclic benzylidene acetal-functionalized graft copolymer via sequential RAFT and ATRP polymerization", Polymer Chemistry, vol. 5, No. 6, Jan. 1, 2014 (Jan. 1, 2014), p. 1852-1865, (5 pages total).

Office Action dated Dec. 10, 2018 by the State Intellectual Property Office of P.R. China in Chinese Patent Application No. 201580018321.7.

STN Database, STN Registry, Feb. 26, 2014. (83 pages total).

Wahl et al; "PEG-tethered guanosine acetal conjugates for the enzymatic synthesis of modified RNA"; Biochemical and Biophysical Research Communications; 2012; vol. 417; No. 4; pp. 1224-1226.

Written Opinion dated Jun. 16, 2015 issued by the International Searching Authority in International Application No. PCT/JP2015/060013 (PCT/ISA237).

Non-Final Office Action dated Jun. 6, 2017 issued by the USPTO in Parent U.S. Appl. No. 15/300,699.

Final Office Action dated Nov. 27, 2017 issued by the USPTO in Parent U.S. Appl. No. 15/300,699.

Non-Final Office Action dated Nov. 28, 2018 issued by the USPTO in Parent U.S. Appl. No. 15/300,699.

Final Office Action dated May 8, 2019 issued by the USPTO in Parent U.S. Appl. No. 15/300,699.

Non-Final Office Action dated Nov. 18, 2019 issued by the USPTO in Parent U.S. Appl. No. 15/300,699.

Final Office Action dated Apr. 10, 2020 issued by the USPTO in Parent U.S. Appl. No. 15/300,699.

HYDROPHILIC POLYMER DERIVATIVE HAVING CYCLIC BENZYLIDENE ACETAL LINKER

CROSS REFERENCE TO RELATED APPLICATIONS

This application is a Continuation Application of U.S. application Ser. No. 15/300,699 filed Sep. 29, 2016, which is a National Stage of International Application No. PCT/JP2015/060013 filed Mar. 30, 2015, which claims priority based on Japanese Patent Application No. 2014-072356 filed Mar. 31, 2014 and Japanese Patent Application No. 2014-193039 filed Sep. 22, 2014, the contents of all of which are incorporated herein by reference in their entirety.

TECHNICAL FIELD

The present invention relates to a hydrophilic polymer derivative which has an acid-hydrolysable acetal linker and is used for chemical modification of a biofunctional molecule, for example, a physiologically active protein, a peptide, an antibody, a nucleic acid or a low molecular weight drug, or a drug carrier, for example, a liposome or a polymer micelle.

BACKGROUND ART

In drug delivery system, the chemical modification of biofunctional molecule or drug carrier with a hydrophilic polymer having low antigenicity is an effective technique for increasing water solubility and bioavailability of the drug or the like and for prolonging circulation time in blood. On the other hand, it is known that the formation of a hydrated layer by the hydrophilic polymer after the drug or the like connected to the hydrophilic polymer is transported to the tissue or site as a target decreases interaction with a cell membrane and inhibits in vivo/intracellular kinetics, for example, uptake into the cell or endosome escape. As to such a problem, an approach to overcome the problem by detaching the hydrophilic polymer chain from the drug and the like at a suitable timing has been performed. Most of the strategies utilize an environmental change at each portion of the living body, for example, reductive environment or the presence or absence of a specific enzyme, as a trigger of the detachment of the hydrophilic polymer chain, and one of them is a technique of utilizing a change in pH.

It is known that the periphery of a tumor tissue in the living body is an acidic environment in comparison with a normal tissue, and the pH of endosomal interior after the drug or the like is introduced into the cell through an endocytosis pathway also gradually decreases. Therefore, for the purpose of selectively detaching the hydrophilic polymer under the acidic environment, a large number of synthesis examples of hydrophilic polymer derivative having an acid-hydrolysable acetal linker introduced into the structure thereof have been reported. However, there is no example in which the hydrolyzability of the acetal linker can be controlled and there are not a few examples in which a problem exists in the method of introducing the acetal linker.

For example, in Patent Document 1, a branched polyethylene glycol derivative in which two chains of polyethylene glycol which is a hydrophilic polymer having low antigenicity are connected through an acetal group derived from various aldehydes or ketones, and a synthetic method thereof are disclosed, but evaluation data of hydrolyzability is not described. Also, the synthetic method described therein is a method for obtaining a polyethylene glycol derivative having an acetal linker by reacting an excess amount of polyethylene glycol with various aldehydes or ketones, so that a large amount of the unreacted polyethylene glycol remains after the reaction. In the case where activation of the polymer terminal is performed using the mixture as a raw material, an impurity in which the terminal of the unreacted polyethylene glycol has also been activated is by-produced. When the activated polyethylene glycol containing such an impurity is used for drug modification, a drug modified with the polyethylene glycol containing no acetal linker is formed as a result, so that a large influence is exerted on the in vivo kinetics and physical properties of the drug. Therefore, it is necessary to remove the polyethylene glycol impurity before the reaction with the drug, but in the case of the production in an industrial scale, there is a possibility that the separation and removal of the polymer impurity causes a severe adverse effect from a technical and cost standpoint.

As another method for obtaining an acetal compound, there is a method of reacting an alcohol with a vinyl ether under acidic conditions. For example, in Non-Patent Document 1, polyethylene glycol derivatives having various functional groups connected through ethylidene acetal linkers are synthesized by reacting vinyl ethers having various functional groups with polyethylene glycol. However, also in the document, evaluation data of hydrolyzability is not shown.

In the synthetic method described in Non-Patent Document 1, since the vinyl ether which is a low-molecular weight compound is used in an excess amount to polyethylene glycol, a large amount of unreacted polyethylene glycol does not remain. However, the acetal group to be introduced by the synthetic method contains an ethylidene acetal structure, the kind of the acetal group which can be introduced is limited. In the case of introducing a benzylidene acetal group, a ketal structure is inevitably formed, and since the ketal structure is sensitive to an acid, a dimer impurity in which two chains of polyethylene glycol are connected through a ketal group is by-produced in a large amount by a ketal exchange reaction in the synthetic method. Therefore, the synthetic method described in Non-Patent Document 1 is difficult to apply to the synthesis of a polyethylene glycol derivative having a benzylidene acetal linker.

On the other hand, in Non-Patent Document 2, several kinds of polyethylene glycol derivatives in which a low-molecular weight model drug is connected through an aliphatic or benzylidene acetal linker are synthesized by synthesizing a unit having an acetal group formed by utilizing a hydroxyl group of the low-molecular weight model drug, and condensing the unit with a separately synthesized activated polyethylene glycol derivative. In this case, although it is shown that a difference in the structure around the acetal group affects the hydrolysis rate, that is, the detaching rate of the polyethylene glycol chain, the correlation between the rate and the structure around the acetal group is not been clarified so that it cannot be said that the hydrolyzability can be controlled. Also, since the method is a method of forming an acetal group by utilizing the hydroxyl group of the low-molecular model drug, it is difficult to use the method in the chemical modification of substance other than the low-molecular weight drug, for example, protein or a drug carrier.

As described above, although there are many examples of hydrophilic polymer derivatives each having an acetal linker introduced into the structure for the purpose of detaching the hydrophilic polymer chain under an acidic environment in the living body, there is no example relating to the hydrophilic polymer derivative in which the hydrolysis rate of the acetal linker, that is, the detaching rate of the hydrophilic polymer chain is accurately controlled at an arbitrary pH.

PRIOR ART DOCUMENTS

Patent Document

Patent Document 1: WO2005/108463

Non-Patent Documents

Non-Patent Document 1: 57th Annual Meeting of The Society of Polymer Science, Japan, Preprints of The Society of Polymer Science, Japan, 57, 1897 (May, 2008)
Non-Patent Document 2: Bioconjugate Chem. 2004, 15, 1254-1263

DISCLOSURE OF THE INVENTION

Problems that the Invention is to Solve

The deviation of pH at each portion of the living body is very small and, for example, although the periphery of a tumor tissue is an acidic environment in comparison with pH 7.4 in normal tissue, the pH thereof is weakly acidic and approximately 6.0. Also, an endosomal interior shows pH 5.5 to 6.0 and is weakly acidic, and the endosomal interior is gradually acidified and approaches pH 4.5 to 5.0 which is the pH of a lysosome. Since an endosome is finally fused with a lysosome, it is required that the drug or the like taken up in the endosome should escape from the endosome at around pH 5.5, in order to avoid degradation thereof by a lysosomal enzyme. Therefore, in the case where it is intended to control in vivo/intracellular kinetics, for example, site-selective cellular uptake and endosome escape of the drug or the like by detaching a hydrophilic polymer chain by utilizing a slight difference in pH at each portion of the living body, for example, the periphery of a tumor tissue or an endosomal interior, it is necessary to accurately control the hydrolysis rate of the acetal linker at the pH of the weakly acidic environment in the living body.

An object of the present invention is to provide a hydrophilic polymer derivative having an acetal linker whose hydrolysis rate at pH of a weakly acidic environment in the living body can be accurately controlled, and which does not liberate a low molecular weight substance other than the hydrophilic polymer chain and the drug or the like connected, more specifically, a low molecular weight aldehyde, at the time of hydrolysis.

Means for Solving the Problems

As a result of the intensive investigations to solve the problem described above, the inventors have developed a hydrophilic polymer derivative having a cyclic benzylidene acetal linker whose hydrolysis rate at pH of a weakly acidic environment in the living body can be accurately controlled, and which does not liberate a low molecular weight substance other than the hydrophilic polymer chain and the drug or the like connected, more specifically, a low molecular weight aromatic aldehyde, at the time of hydrolysis.

The feature of the invention resides in that a chemically reactive functional group and a hydrophilic polymer are connected through a cyclic benzylidene acetal linker having substituent(s). By appropriately selecting the kind and position of the substituent(s) on the benzene ring of the cyclic benzylidene acetal linker, the degrees of electron density and steric hindrance around the acetal group which affect the hydrolysis rate of the acetal linker can be adjusted. Based on the feature, it is possible to impart a desired hydrolysis rate to the acetal linker and it becomes possible to detach the hydrophilic polymer chain at an arbitrary rate from the drug or the like which is connected to the hydrophilic polymer derivative.

Another feature of the invention resides in that the hydrophilic polymer and a benzene ring of the cyclic benzylidene acetal linker are connected through a bond which is stable in the living body. Based on the feature, the invention has an advantage in that liberation of a low molecular weight substance other than the hydrophilic polymer chain and the drug or the like connected, more specifically, a low molecular weight aromatic aldehyde can be avoided at the time of hydrolysis.

The hydrophilic polymer derivative of the invention can be synthesized by performing a coupling reaction between a linker compound, into which a cyclic benzylidene acetal group having substituent(s) is introduced, and a hydrophilic polymer intermediate. Therefore, it is not necessary to use such an excess amount of the hydrophilic polymer for forming the acetal group as in Patent Document 1 and the removal of the unreacted hydrophilic polymer impurity is not required, so that it is easy to perform the production on an industrial scale. Moreover, there is no limitation on the kind of the acetal group which can be introduced and a benzylidene acetal group which cannot be introduced by the synthetic method of Non-Patent Document 1 can also be introduced. Furthermore, unlike Non-Patent Document 2, in the hydrophilic polymer derivative of the invention, since various functional groups can be introduced into the terminal of the acetal linker, it is possible to form a covalent bond with various biofunctional molecules and drug carriers.

That is, the invention includes the following items.

[1] A hydrophilic polymer derivative having a cyclic benzylidene acetal linker represented by formula (1):

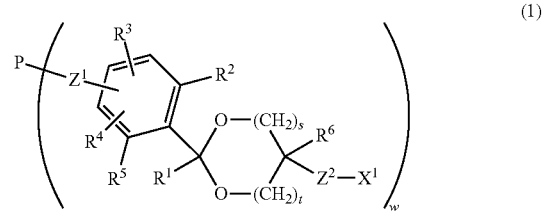

wherein $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $X^1$ is a chemically reactive functional group; P is a hydrophilic polymer; s is 1 or 2, t is 0 or 1, and s+t is 1 or 2; w is an integer of 1 to 8; and $Z^1$ and $Z^2$ are each independently a selected divalent spacer.

[2] The hydrophilic polymer derivative of [1], wherein s is 1 and t is 0, $R^2$ and $R^5$ are each a hydrogen atom, and a sum ($\Sigma\sigma$) of substituent constants ($\sigma$) in $R^3$, $R^4$ and $P—Z^1$ satisfies $-0.30 \leq \Sigma\sigma \leq 1.05$.

[3] The hydrophilic polymer derivative of [1], wherein s is 1 and t is 0, at least one of $R^2$ and $R^5$ is the substituent described above, and a sum ($\Sigma\sigma$) of substituent constants ($\sigma$) in $R^3$, $R^4$ and $P—Z^1$ satisfies $-1.71 \leq \Sigma\sigma \leq 0.88$.

[4] The hydrophilic polymer derivative of [1], wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and P—$Z^1$ satisfies $-0.19 \leq \Sigma\sigma \leq 0.57$.

[5] The hydrophilic polymer derivative of [1], wherein s is 1 and t is 1, or s is 2 and t is 0, at least one of $R^2$ and $R^5$ is the substituent described above, and a sum ($\Sigma\sigma$) of substituent constants ($\sigma$) in $R^3$, $R^4$ and P—$Z^1$ satisfies $-0.98 \leq \Sigma\sigma \leq 0.48$.

[6] The hydrophilic polymer derivative of any one of [1] to [5], wherein $X^1$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[7] The hydrophilic polymer derivative of any one of [1] to [6], wherein $X^1$ is selected from the group consisting of formula (a), formula (b), formula (c), formula (d), formula (e), formula (f), formula (g), formula (h), formula (i), formula (j), formula (k), formula (l), formula (m) and formula (n).

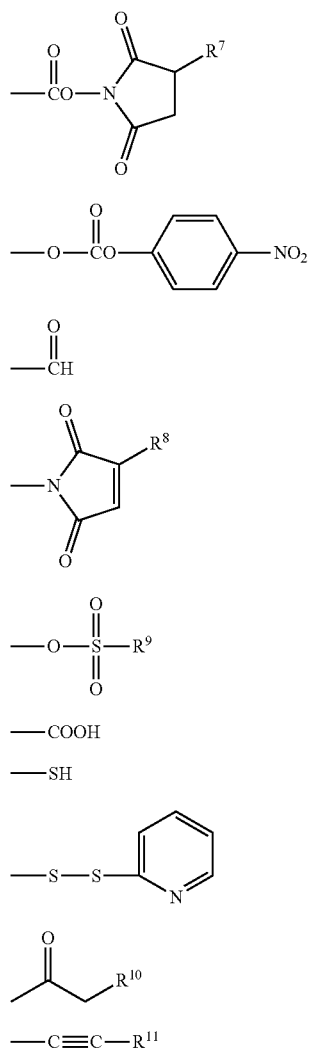

 (k)

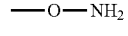 (l)

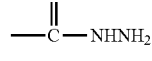 (m)

 (n)

wherein $R^7$ is a hydrogen atom or a sulfo group; $R^8$ and $R^1$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from a chlorine atom, a bromine atom and an iodine atom.

[8] The hydrophilic polymer derivative of any one of [1] to [7], wherein $Z^1$ and $Z^2$ are each independently an ether bond, an ester bond, a carbonate bond, a urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

[9] The hydrophilic polymer derivative of any one of [1] to [8], wherein P is a linear polyethylene glycol having a hydrocarbon group or a chemically reactive functional group at its terminal.

[10] The hydrophilic polymer derivative of [9], wherein w is 1, and P is represented by formula (2):

wherein Y is a hydrocarbon group having from 1 to 24 carbon atoms; and n is an integer of 3 to 2,000.

[11] The hydrophilic polymer derivative of [9], wherein w is 1, and P is represented by formula (3):

wherein $X^2$ is a chemically reactive functional group different from $X^1$; $Z^3$ is a divalent spacer; and n is an integer of 3 to 2,000.

[12] The hydrophilic polymer derivative of any one of [1] to [8], wherein P is a branched polyethylene glycol having a hydrocarbon group or a chemically reactive functional group different from $X^1$ at its terminal.

[13] The hydrophilic polymer derivative of [12], wherein w is 1, and P is represented by formula (4):

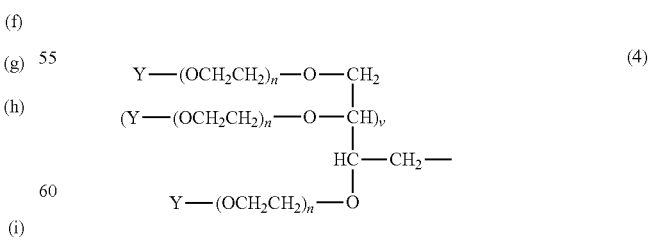

wherein Y is a hydrocarbon group having from 1 to 24 carbon atoms; n is an integer of 3 to 1,000; and v is 0 or 2.

[14] The hydrophilic polymer derivative of [12], wherein w is 1, and P is represented by formula (5):

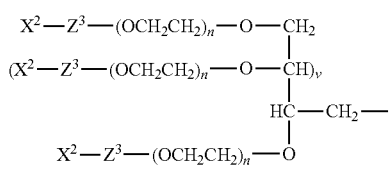

(5)

wherein $X^2$ is a chemically reactive functional group different from $X^1$; $Z^3$ is a divalent spacer; n is an integer of 3 to 1,000; and v is 0 or 2.

[15] The hydrophilic polymer derivative of [12], wherein w is v+2, and P is represented by formula (6):

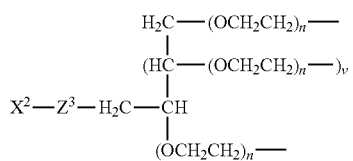

(6)

wherein $X^2$ is a chemically reactive functional group different from $X^1$; $Z^3$ is a divalent spacer; n is an integer of 3 to 1,000; and v is 0 or 2.

The hydrophilic polymer derivative of any one of [11], [14] and [15], wherein $X^2$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

The hydrophilic polymer derivative of any one of [11], [14] and [15], wherein $X^2$ is selected from the group consisting of formula (a), formula (b), formula (c), formula (d), formula (e), formula (f), formula (g), formula (h), formula (i), formula (j), formula (k), formula (l), formula (m) and formula (n):

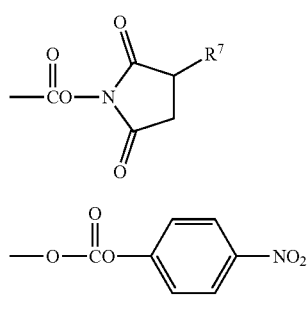

(a)

(b)

(c)

(d)

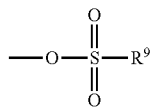

(e)

—COOH (f)

—SH (g)

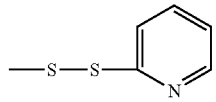

(h)

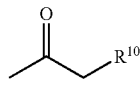

(i)

—C≡C—$R^{11}$ (j)

—$NH_2$ (k)

—O—$NH_2$ (l)

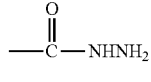

(m)

—$N_3$ (n)

wherein $R^7$ is a hydrogen atom or a sulfo group; $R^8$ and $R^1$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from a chlorine atom, a bromine atom and an iodine atom.

[18] The hydrophilic polymer derivative of any one of [11], [14] and [15], wherein $Z^3$ is an ether bond, an ester bond, a carbonate bond, a urethane bond, an amide bond, a secondary amino group, an alkylene group containing any of these bonds and group, a single bond or an alkylene group, and in a case where $Z^3$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

[19] The hydrophilic polymer derivative of any one of [1] to [8], wherein P is polyethylene glycol having the number of terminals of 2 to 8, all the terminals of the polyethylene glycol constituting P are each connected to $Z^1$, and w is equal to the number of terminals of the polyethylene glycol.

[20] The hydrophilic polymer derivative of [19], wherein P is selected from the group consisting of formula (r), formula (s), formula (t), formula (u) and formula (v):

—$CH_2CH_2(OCH_2CH_2)_n$— (r)

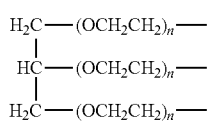

(s)

-continued

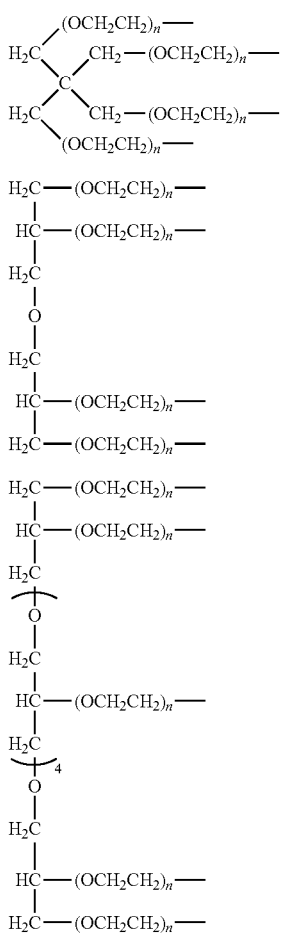

wherein n is an integer of 3 to 2,000, and w is 2 when P is represented by formula (r), w is 3 when P is represented by formula (s), w is 4 when P is represented by formula (t), w is 4 when P is represented by formula (u), and w is 8 when P is represented by formula (v).

[21] A cyclic benzylidene acetal linker compound represented by formula (55):

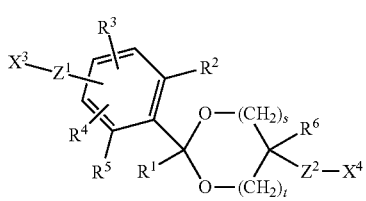

(55)

wherein $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; $X^3$ and $X^4$, which may be the same or different, are each a chemically reactive functional group; s is 1 or 2, t is 0 or 1, and s+t is 1 or 2; and $Z^1$ and $Z^2$ are each independently a selected divalent spacer.

[22] The cyclic benzylidene acetal linker compound of [21], wherein s is 1 and t is 0, $R^2$ and $R^5$ are each a hydrogen atom, and a sum ($\Sigma\sigma$) of substituent constants ($\sigma$) in $R^3$, $R^4$ and $X^3$—$Z^1$ satisfies $-0.30 \leq \Sigma\sigma \leq 1.05$.

The cyclic benzylidene acetal linker compound of [21], wherein s is 1 and t is 0, at least one of $R^2$ and $R^5$ is the substituent described above, and a sum ($\Sigma\sigma$) of substituent constants ($\sigma$) in $R^3$, $R^4$ and $X^3$—$Z^1$ satisfies $-1.71 \leq \Sigma\sigma \leq 0.88$.

[24] The cyclic benzylidene acetal linker compound of [21], wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and $X^3$—$Z^1$ satisfies $-0.19 \leq \Sigma\sigma \leq 0.57$.

[25] The cyclic benzylidene acetal linker compound of [21], wherein s is 1 and t is 1, or s is 2 and t is 0, at least one of $R^2$ and $R^5$ is the substituent described above, and a sum ($\Sigma\sigma$) of substituent constants ($\sigma$) in $R^3$, $R^4$ and $X^3$—$Z^1$ satisfies $-0.98 \leq \Sigma\sigma \leq 0.48$.

[26] The cyclic benzylidene acetal linker compound of any one of [21] to [25], wherein $X^3$ and $X^4$ are each selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group, an azide group and hydroxy group.

[27] The cyclic benzylidene acetal linker compound of any one of [21] to [26], wherein $X^3$ and $X^4$ are each selected from the group consisting of formula (a), formula (b), formula (c), formula (d), formula (e), formula (f), formula (g), formula (h), formula (i), formula (j), formula (k), formula (l), formula (m), formula (n) and formula (o).

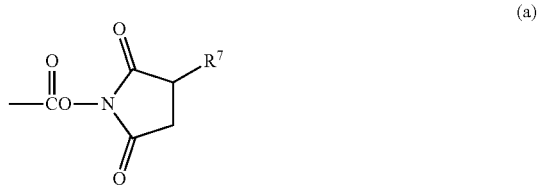
(a)

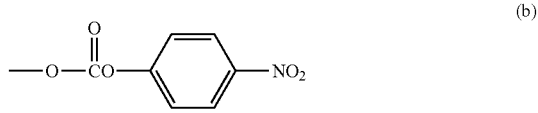
(b)

(c)

(d)

(e)

(f)

(g)

(h)

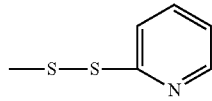

-continued

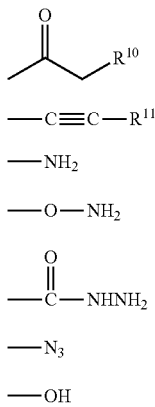

—C≡C—R$^{11}$ (j)

—NH$_2$ (k)

—O—NH$_2$ (l)

$$-\overset{\overset{\displaystyle O}{\|}}{C}-NHNH_2$$ (m)

—N$_3$ (n)

—OH (o)

wherein R$^7$ is a hydrogen atom or a sulfo group; R$^8$ and R$^{11}$ are each independently a hydrogen atom or a hydrocarbon group having from 1 to 5 carbon atoms; R$^9$ is a hydrocarbon group having from 1 to 10 carbon atoms which may contain a halogen atom; and R$^{10}$ is a halogen atom selected from a chlorine atom, a bromine atom and an iodine atom.

[28] The cyclic benzylidene acetal linker compound of any one of [21] to [27], wherein Z$^1$ and Z$^2$ are each independently an ether bond, an ester bond, a carbonate bond, a urethane bond, an amide bond, a secondary amino group, an alkylene group containing any of these bonds and group, a single bond or an alkylene group, and in a case where at least one of Z$^1$ and Z$^2$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

[29] The cyclic benzylidene acetal linker compound of any one of [21] to [28], wherein the functional group constituting any one of X$^3$ and X$^4$ contains a protective group.

Advantage of the Invention

In the hydrophilic polymer derivative having a cyclic benzylidene acetal linker according to the invention, the hydrolysis rate of the cyclic benzylidene acetal linker can be controlled according to the pH of a weakly acidic environment in the living body and it is possible to selectively detach the hydrophilic polymer chain from the drug or the like connected to the hydrophilic polymer derivative at the pH of the target portion. Therefore, it is possible to fundamentally eliminate problems, for example, inhibition of intracellular uptake and endosome escape resulting from hydrated layer formation of a hydrophilic polymer which are disadvantages of the conventional hydrophilic polymer modification by detaching the hydrophilic polymer chain after a biofunctional molecule or drug carrier connected to the hydrophilic polymer derivative has been transported to the tissue or site as a target. That is, by using the hydrophilic polymer derivative in the chemical modification of the drug or the like, it is possible to impart only the advantages of hydrophilic polymer modification, for example, an increase in water solubility and bioavailability and prolongation of circulation time in blood, without preventing the expression of the original function of the drug or the like.

Moreover, since in the hydrophilic polymer derivative, the hydrophilic polymer and a benzene ring of the cyclic benzylidene acetal linker are connected through a bond which is stable in the living body, liberation of a low molecular weight substance other than the hydrophilic polymer chain and the drug or the like connected, more specifically, a low molecular weight aromatic aldehyde is avoided at the time of hydrolysis so that the influence due to the low molecular weight substance can be eliminated.

MODE FOR CARRYING OUT THE INVENTION

Figure 1:
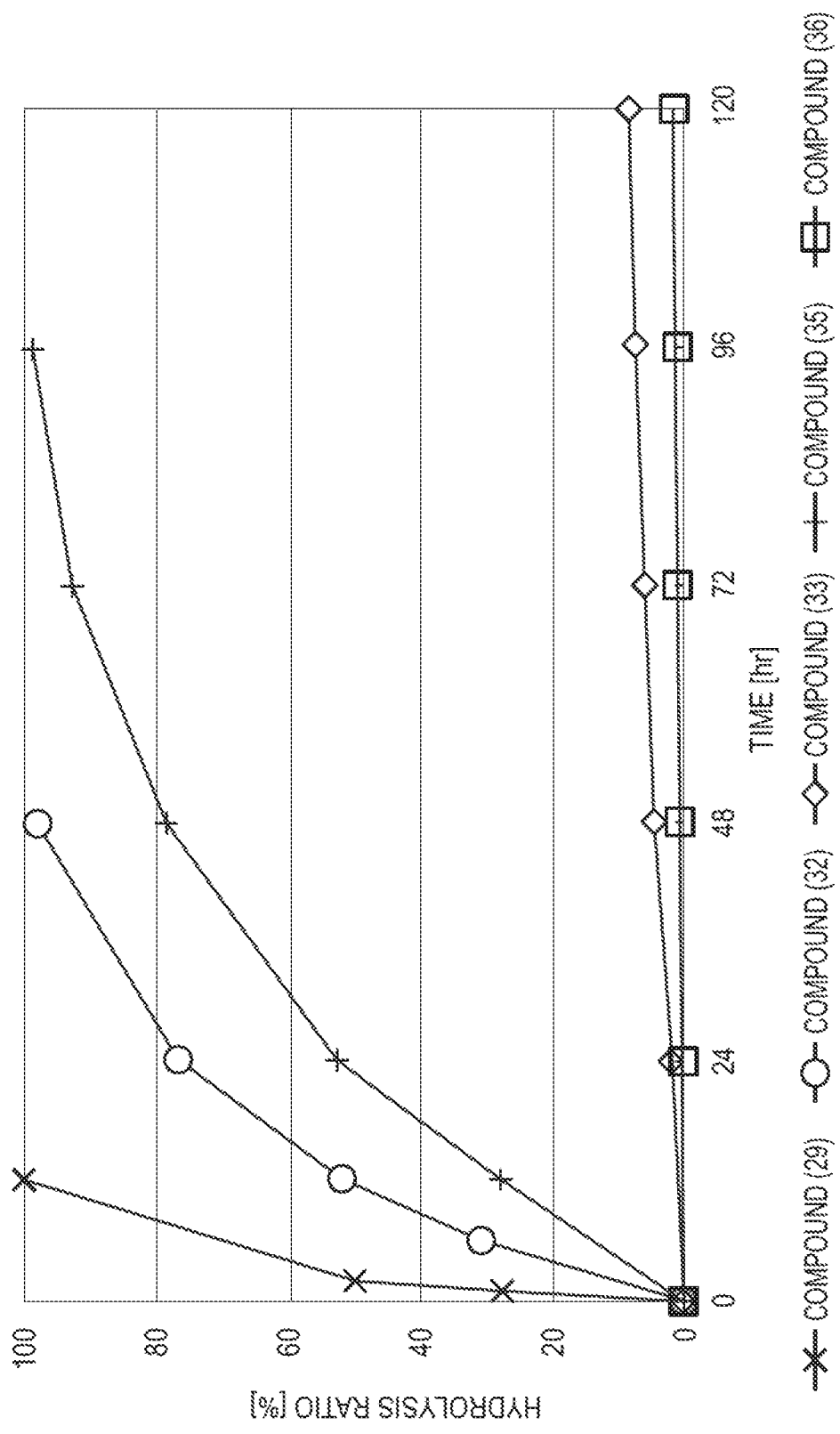
FIG. 1 shows results of the hydrolysis test in MES deuterated water buffer at pD 5.5 at 37° C. using the compounds of formula (29), formula (32), formula (33), formula (35) and formula (36) described in Examples.

The invention will be described in detail hereinafter.

The term "acetal" as used in the specification means both of an acetal structure derived from an aldehyde and an acetal structure derived from a ketone, that is, a ketal structure.

The term "cyclic acetal" as used in the invention means both of a 1,3-dioxolane structure of a 5-membered ring which is s is 1 and t is 0 in formula (1) and a 1,3-dioxane structure of a 6-membered ring which is s is 1 and t is 1 or s is 2 and t is 0 in formula (1)

Each of R$^1$ and R$^6$ in formula (1) of the invention is a hydrogen atom or a hydrocarbon group, a number of carbon atoms of the hydrocarbon group is preferably 10 or less, and specific examples of the hydrocarbon group include a methyl group, an ethyl group, a propyl group, an isopropyl group, a tert-butyl group, a phenyl group and a benzyl group. A preferred embodiment of R$^1$ is a hydrogen atom or a methyl group, and a hydrogen atom is more preferred.

The benzene ring in formula (1) of the invention may have a plurality of substituents. By appropriately selecting the kind, the position and the degree of electron-donating property and electron-withdrawing property of the substituents on the benzene ring, it is possible to adjust the degrees of electron density and steric hindrance around the acetal group which affects the hydrolysis rate of the cyclic acetal linker. This makes it possible to impart a desired hydrolysis rate to the cyclic acetal linker.

In the specification, the substituent(s) on the benzene ring in formula (1) is described using the "substituent constant (a)" which means the substituent constant in the Hammett's rule which quantifies the effect of the substituent on the reaction rate or equilibrium of benzene derivative. However, as is known, the Hammett's rule is applied only to a para-substituted or meta-substituted benzene derivative and cannot be applied to an ortho-substituted benzene derivative which is affected by steric hindrance. Therefore, in the case of ortho-substituted benzene derivative, the substituent constant means the substituent constant in the Taft's equation which extends the Hammett's rule described above.

In the para-substituted or meta-substituted benzene derivative described above, the Hammett's rule is represented by the following formula (7).

$$\log(k/k_0)=\rho\sigma \qquad (7)$$

wherein k is a rate constant or equilibrium constant in an arbitrary reaction of para-substituted or meta-substituted benzene derivative, k$_0$ is a rate constant or equilibrium constant in the case where the benzene derivative does not have a substituent, that is, the substituent is a hydrogen atom, ρ is a reaction constant, and a is a substituent constant.

The reaction constant (ρ) in formula (7) described above is a constant which is determined depending on reaction conditions, for example, the kind of reaction, temperature or solvent, and can be calculated from the slope of Hammett plots. In the acid hydrolysis reaction of the hydrophilic polymer derivative having a cyclic benzylidene acetal linker of the invention, in the case of 1,3-dioxolane structure, the constant is calculated as "ρ=−2.7" from the results of the hydrolysis tests performed for the compounds of formula (29), formula (32) and formula (33) described in Examples. Also, in the case of 1,3-dioxane structure, the constant is calculated as "ρ=−4.8" from the results of the hydrolysis tests performed for the compounds of formula (35) and formula (36).

The substituent constant (a) in formula (7) described above is a constant which is determined only depending on the kind and position of the substituent, regardless of the kind of reaction. In the case where no substituent is present, that is, the substituent is a hydrogen atom, the constant is "0". The term "electron-withdrawing" as used in the specification means the case where a is a positive value and the term "electron-donating" means the case where a is a negative value.

As described above, the Hammett's rule is applied only to para-substituted or meta-substituted benzene derivative and cannot be applied to the case of ortho-substituted benzene derivative which is affected by steric hindrance. Therefore, it is the Taft's equation that the effect of such steric hindrance is introduced as a factor of the position, that is, a position constant (Es) of the substituent, to extend the Hammett's rule so that it can also be applied to the case of the ortho-substituted benzene derivative. The Taft's equation is represented by the following formula (8).

$$\log(k/k_0)=\rho^*\sigma^*+Es \qquad (8)$$

wherein k is a rate constant or equilibrium constant in an arbitrary reaction of para-substituted or meta-substituted benzene derivative, $k_0$ is a rate constant or equilibrium constant in the case where the benzene derivative does not have a substituent, that is, the substituent is a hydrogen atom, $\rho^*$ is a reaction constant, $\sigma^*$ is a substituent constant, and Es is a position constant of the substituent.

As is known, since the reaction constant (ρ) of para-substituted or meta-substituted benzene derivative and the reaction constant ($\rho^*$) of ortho-substituted benzene derivative are approximately equal, it is defined in the specification that ρ and $\rho^*$ are the same. Since the substituent constant ($\sigma^*$) in the ortho position is similar to the substituent constant in the para position as described, for example, in "Charton, M. Can. J. Chem. 1960, 38, 2493-2499", to the substituent constant in the ortho position in the specification is applied a corresponding substituent constant in the para position.

The substituent constant (a) in the para position or the meta position is described in "Hansch, C.; Leo, A.; Taft, R. W. Chem. Rev. 1991, 91, 165-195", and with respect to a substituent in which the substituent constant (a) is unknown the constant can be measured and determined by the method described in "Hammett, L. P. Chem. Rev. 1935, 17(1), 125-136". Moreover, the position constant (Es) is described in "Unger, S. H.; Hansch, C. Prog. Phys. Org. Chem. 1976, 12, 91-118". However, as to Es as used in the specification, a hydrogen atom is defined as "0".

In formula (1), in the case where a plurality of substituents are present on the benzene ring, it is defined that additivity is established for the substituent constant (a) and the position constant (Es) thereof, and the sum of a is represented by "Σσ" and the sum of Es is represented by "ΣEs".

$Z^1$ is connected to the benzene ring of the cyclic benzylidene acetal and P—$Z^1$ is also a substituent of the benzene ring. The substituent constant of P—$Z^1$ can be determined by separately measuring the composition and polymerization degree of P and combination thereof with $Z^1$, but, since the substituent constant of P—$Z^1$ is substantially affected largely by the structure in the vicinity of the connecting portion to the benzene ring, the effect of the other portions is so small as to be ignored. Therefore, it is possible to use a known substituent constant of a structure similar to the structure in the vicinity of the connecting portion to the benzene ring in place of separately measuring the substituent constant as to P—$Z^1$.

It is defined that the substituent constant of P—$Z^1$ in the specification can be substituted with a substituent constant of a structure in which atom(s) other than the second atom connected to the third atom counted from the atom connected to the benzene ring the backbone atoms of the main chain of P—$Z^1$ are substituted with hydrogen atom(s). However, in the case where, when the atom is substituted with a hydrogen atom, a carboxy group is formed, it is defined that the substituent constant of P—$Z^1$ can be substituted with a substituent constant of a structure in which the atom is substituted with a methyl group in place of a hydrogen atom.

Specific examples of the structure of the connecting portion to the benzene ring in P—$Z^1$ and the structure for the substitution are shown below. In the case of (r1) shown below, wherein the connecting portion to the benzene ring in P—$Z^1$ is an ether bond, a substituent constant of (r2) shown below is applied. In the cases of (r3) and (r5) shown below, wherein the connecting portion to the benzene ring in P—$Z^1$ is an amide bond, substituent constants of (r4) and (r6) shown below are applied, respectively. In the case of (r7) shown below, wherein the connecting portion to the benzene ring in P—$Z^1$ is a urethane bond, a substituent constant of (r8) shown below is applied.

Structure of Connecting Portion to Benzene Ring                Structure for Substitution

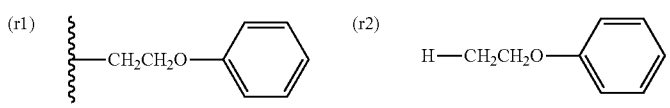

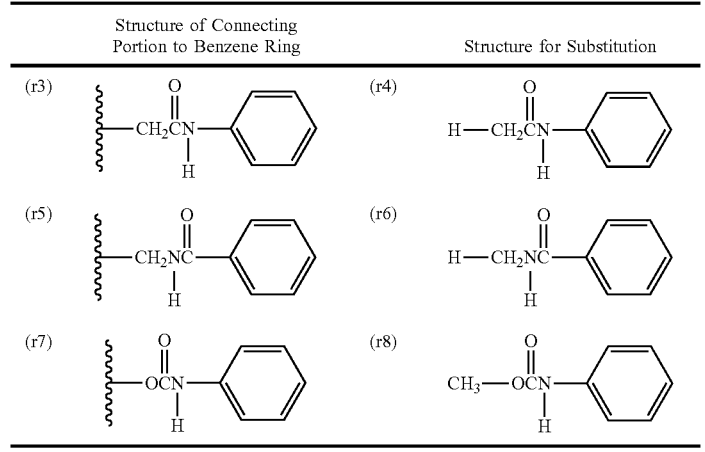

As to the appropriate hydrolysis rate of the hydrophilic polymer derivative having a cyclic benzylidene acetal linker of the invention, hydrolysis half-life ($t_{1/2}$) in a buffer at pH 5.5 and 37° C. is preferably in the range from 1 hour to 6 months, more preferably in the range from 1 hour to 1 month, and still more preferably in the range from 1 hour to 24 hours. In the specification, using a numerical value derived from the compound of formula (32) described in Examples in which $t_{1/2}$ under the hydrolysis conditions described above is 12 hours, a suitable range of the sum ($\Sigma\sigma$) of substituent constants in the case where a 1,3-dioxolane structure is included is defined. When $\log(k/k_0)$ for the compound of formula (32) is calculated using equation (7) above, the following equation (9) is obtained. However, as defined above, P—$Z^1$ in the compound of formula (32) is substituted with an ethoxy group ($CH_3CH_2O$—).

$$\log(k/k_0) = -2.7 \times (0.34 - 0.24) = -0.27 \quad (9)$$

In the case where $R^2$ and $R^5$ in formula (1) are hydrogen atoms, when $\log(k'/k_0)$ is calculated by taking the rate constant at the time when $t_{1/2}$ is 24 hours as k' using equation (9) and equation (7) above, the following equation (10) is obtained.

$$\log(k'/k) = \log\{(12/24)k/k\} = -0.30$$

When the equation is modified, $$\log(k'/k) = \log[(k'/k_0)/(k/k_0)] = -0.30$$

$$\log(k'/k_0) - \log(k/k_0) = -0.30$$

When equation (9) above is substituted, $$\log(k'/k_0) - (-0.27) = -0.30$$

$$\log(k'/k_0) = -0.57 \quad (10)$$

Here, when the sum ($\Sigma\sigma$) of the substituent constants is calculated using equation (10) and equation (7) above, the following equation (11) is obtained.

$$\log(k'/k_0) = -2.7 \times \Sigma\sigma = -0.57$$

$$\Sigma\sigma = 0.21 \quad (11)$$

Similarly, in the case where $R^2$ and $R^5$ in formula (1) are hydrogen atoms, when $\log(k''/k_0)$ is calculated by taking the rate constant at the time when $t_{1/2}$ is 1 hour as k'', the following equation (12) is obtained.

$$\log(k''/k) = \log(12k/k) = 1.08$$

When the equation is modified, $$\log(k''/k) = \log[(k''/k_0)/(k/k_0)] = 1.08$$

$$\log(k''/k_0) - \log(k/k_0) = 1.08$$

When equation (9) above is substituted, $$\log(k''/k_0) - (-0.27) = 1.08$$

$$\log(k''/k_0) = 0.81 \quad (12)$$

Here, when the sum ($\Sigma\sigma$) of the substituent constants is calculated using equation (12) and equation (7) above, the following equation (13) is obtained.

$$\log(k''/k_0) = -2.7 \times \Sigma\sigma = 0.81$$

$$\Sigma\sigma = -0.30 \quad (13)$$

From equation (11) and equation (13), in the case where formula (1) includes a 1,3-dioxolane structure and $R^2$ and $R^5$ are hydrogen atoms, when the range of $\Sigma\sigma$ satisfies $-0.30 \leq \Sigma\sigma \leq 0.21$, $t_{1/2}$ of the hydrophilic polymer derivative is represented by 1 hour $\leq t_{1/2} \leq 24$ hours. Similarly, when the ranges of $\Sigma\sigma$ at 1 hour $\leq t_{1/2} \leq 1$ month and 1 hour $\leq t_{1/2} \leq 6$ months are calculated, $-0.30 \leq \Sigma\sigma \leq 0.76$ at the time of 1 hour $\leq t_{1/2} \leq 1$ month and $-0.30 \leq \Sigma\sigma \leq 1.05$ at the time of 1 hour $\leq t_{1/2} \leq 6$ months, respectively.

The substituent which can be used in the invention is a substituent which does not inhibit the acetalization reaction of the cyclic benzylidene acetal linker compound, the coupling reaction of the cyclic benzylidene acetal linker compound with the hydrophilic polymer intermediate and the terminal functional group conversion reaction of the hydrophilic polymer derivative in the synthesis process of the hydrophilic polymer derivative, and further the bond-forming reaction between the hydrophilic polymer derivative and the drug or the like.

The substituent may be any of electron-withdrawing substituent and electron-donating substituent as far as it satisfies the conditions described above, and the substituents may be used individually or in combination. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para-position and ortho-position includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

In the case where formula (1) includes a 1,3-dioxolane structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 1 hour$\leq t_{1/2} \leq$24 hours, 1 hour$\leq t_{1/2} \leq$1 month, and 1 hour$\leq t_{1/2} \leq$6 months are calculated by using Taft's equation (8), respectively. As a result, it is found that $-1.71 \leq \Sigma\sigma \leq 0.04$ at the time of 1 hour$\leq t_{1/2} \leq$24 hours, $-1.71 \leq \Sigma\sigma \leq 0.59$ at the time of 1 hour$\leq t_{1/2} \leq$1 month, and $-1.71 \leq \Sigma\sigma \leq 0.88$ at the time of 1 hour$\leq t_{1/2} \leq$6 months, respectively.

In the case where formula (1) includes a 1,3-dioxolane structure and $R^2$ and $R^5$ are hydrogen atoms, for example, a preferred embodiment which satisfies $-0.30 \leq \Sigma\sigma \leq 0.21$ at the time of 1 hour$\leq t_{1/2} \leq$24 hours is described below. However, the substituents shown herein means $R^3$ and $R^4$ and the structure used in place of $P\text{—}Z^1$ according to the definition described above. In the preferred embodiment, one of the meta-positions in formula (1) is a methoxy group, an ethoxy group or an acetamide group, and more preferably an ethoxy group or an acetamide group. In another preferred embodiment, the para-position in formula (1) is a methoxy group or an ethoxy group and one of the meta-positions is a substituent independently selected from the group consisting of a fluorine atom, a chlorine atom, a bromine atom and an iodine atom, and more preferably the para-position is an ethoxy group and one of the meta-positions is a fluorine atom or a chlorine atom. In still another preferred embodiment, one of the para-position and the meta-position in formula (1) is a methoxy group, an ethoxy group or an acetamide group, and more preferably a methoxy group or an ethoxy group.

Further, in the case where formula (1) includes a 1,3-dioxolane structure and at least one of $R^2$ and $R^5$ is a substituent other than a hydrogen atom, for example, a preferred embodiment which satisfies $-1.71 \leq \Sigma\sigma \leq 0.04$ at the time of 1 hour$\leq t_{1/2} \leq$24 hours is described below. However, the substituents shown herein means $R^3$ and $R^4$ and the structure used in place of $P\text{—}Z^1$ according to the definition described above. In the case where one of $R^2$ and $R^5$ in formula (1) is a fluorine atom, a methyl group or an ethyl group and the other is a hydrogen atom, the para-position is preferably an ethoxy group or an acetamide group, and more preferably an ethoxy group. In the case where one of $R^2$ and $R^5$ in formula (1) is a methoxy group and the other is a hydrogen atom, the para-position is preferably a substituent selected from the group consisting of a methoxymethyl group and an acetamide group, and more preferably an acetamide group.

Moreover, using a numerical value derived from the compound of formula (35) described in Examples in which the hydrolysis half-life ($t_{1/2}$) in a buffer at pH 5.5 and 37° C. is 24 hours, a suitable range of the sum ($\Sigma\sigma$) of substituent constants in the case where formula (1) includes a 1,3-dioxane structure can be defined.

In the case where formula (1) includes a 1,3-dioxane structure and $R^2$ and $R^5$ are hydrogen atoms, when the range of $\Sigma\sigma$ satisfies $-0.19 \leq \Sigma\sigma \leq 0.10$, $t_{1/2}$ of the hydrophilic polymer derivative is represented by 1 hour$\leq t_{1/2} \leq$24 hours. Similarly, when the ranges of $\Sigma\sigma$ at 1 hour$\leq t_{1/2} \leq$1 month and 1 hour$\leq t_{1/2} \leq$6 months are calculated, $-0.19 \leq \Sigma\sigma \leq 0.41$ at the time of 1 hour$\leq t_{1/2} \leq$1 month and $-0.19 \leq \Sigma\sigma \leq 0.57$ at the time of 1 hour$\leq t_{1/2} \leq$6 months, respectively.

Further, in the case where formula (1) includes a 1,3-dioxone structure and at least one of $R^2$ and $R^5$ is a substituent other than a hydrogen atom, using the position constants ($\Sigma\sigma$) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 1 hour$\leq t_{1/2} \leq$24 hours, 1 hour$\leq t_{1/2} \leq$1 month, and 1 hour$\leq t_{1/2} \leq$6 months are calculated by using Taft's equation (8), respectively. As a result, it is found that $-0.98 \leq \Sigma\sigma \leq 0.00$ at the time of 1 hour$\leq t_{1/2} \leq$24 hours, $-0.98 \leq \Sigma\sigma \leq 0.31$ at the time of 1 hour$\leq t_{1/2} \leq$1 month, and $-0.98 \leq \Sigma\sigma \leq 0.48$ at the time of 1 hour$\leq t_{1/2} \leq$6 months, respectively.

As described above, the kind and position of the substituent(s) suitable for imparting the desired hydrolyzability to the hydrophilic polymer derivative having a cyclic benzylidene acetal linker of the invention can be reasonably set by performing the calculation described above using equation (7) and equation (8).

$X^1$ in formula (1) of the invention is not particularly limited as long as it is a functional group which forms a covalent bond upon a reaction with a functional group present in a biofunctional molecule, for example, a physiologically active protein, peptide, an antibody, a nucleic acid or a low molecular drug, or a drug carrier, for example, a liposome or a polymer micelle, which is the object of chemical modification. For example, the functional groups include those described in "Harris, J. M. Poly(Ethylene Glycol) Chemistry; Plenum Press: New York, 1992", "Hermanson, G. T. Bioconjugate Techniques, 2nd ed.; Academic Press: San Diego, Calif., 2008", "PEGylated Protein Drugs: Basic Science and Clinical Applications; Veronese, F. M., Ed.; Birkhauser: Basel, Switzerland, 2009" and the like.

Preferred examples of $X^1$ include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, ahydrazide group and an azide group. More specifically, the functional group capable of forming a covalent bond upon a reaction with an amino group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group, an amino group, an oxyamino group or a hydrazide group, the functional group capable of forming a covalent bond upon a reaction with an alkynyl group of the biofunctional molecules is a thiol group or an azide group, and the functional group capable of forming a covalent bond upon a reaction with an azide group of the biofunctional molecule is an alkynyl group.

The term "active ester" as referred to herein indicates an activated carboxy group represented by formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents a leaving group same as described above.

In a preferred embodiment of the invention, $X^1$ is a group represented by group (I), group (II), group (III), group (IV) or group (V).

Group (I): Functional group capable of forming a covalent bond upon a reaction with an amino group of the biofunctional molecule (a), (b), (c), (d), (e) and (f) shown below:

Group (II): Functional group capable of forming a covalent bond upon a reaction with a thiol group of the biofunctional molecule (a), (b), (c), (d), (e), (f), (g), (h), (i) and (j) shown below:

Group (III): Functional group capable of forming a covalent bond upon a reaction with an aldehyde group or a carboxy group of the biofunctional molecule (g), (k), (l) and (m) shown below:

Group (IV): Functional group capable of forming a covalent bond upon a reaction with an alkynyl group of the biofunctional molecule (g), (k), (l), (m) and (n) shown below:

Group (V): Functional group each capable of forming a covalent bond upon a reaction with an azide group of the biofunctional molecule (j) shown below:

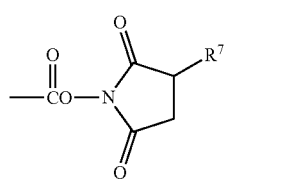

(a)

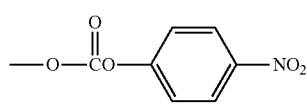

(b)

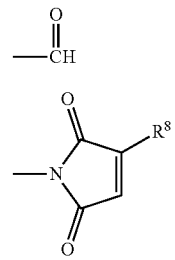

(c)

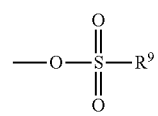

(d)

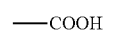

(e)

(f)

—COOH

(g)

—SH

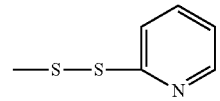

(h)

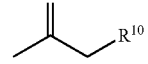

(i)

(j)

—C≡C—$R^{11}$ (k)

—$NH_2$ (l)

—O—$NH_2$ (m)

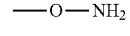

(n)

—$N_3$

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from a chlorine atom, a bromine atom and an iodine atom.

$Z^1$ in formula (1) of the invention is a divalent spacer between the benzene ring of the cyclic benzylidene acetal group and the hydrophilic polymer chain, and $Z^2$ is a divalent spacer between the functional group $X^1$ and the cyclic benzylidene acetal group. These are composed of covalent bonds, are not particularly limited as long as they are more stable to acid hydrolysis than the cyclic benzylidene acetal group, and are preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. For example, in the case where it is intended to connect the functional group $X^1$ in a hydrophobic environment, for example, the inside of a protein, p and q are preferably large, and in the case where it is intended to connect it in a hydrophilic environment, p and q are preferably small. However, in the case where at least one of $Z^1$ and $Z^2$ is an ether bond, an ester bond, a carbonate bond, an urethane bond, an amide bond, a secondary amino group or an alkylene group containing any of these bonds and group and a plurality of identical structural units are connected, a number of the structural units described above is 2 or less.

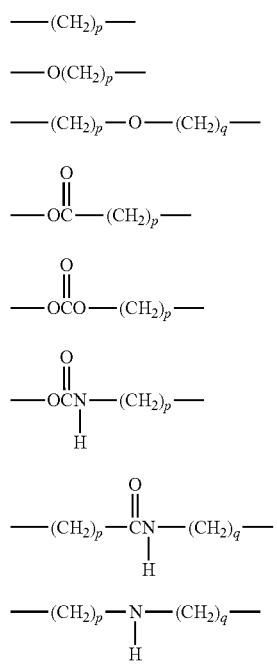

P in formula (1) of the invention is a hydrophilic polymer and specific examples thereof include polyalkylene glycol, polyoxazoline, polycarbonate, polyurethane, polyvinyl alcohol, polyacrylate, polymethacrylate, polyacrylamide, polyvinylpyrrolidone, polylactic acid, polyglycolic acid, polyamino acid and copolymers derived from the polymers described above, and P is preferably polyalkylene glycol, and more preferably polyethylene glycol.

The term "polyethylene glycol" as used in the specification means both of polyethylene glycol having a molecular weight distribution obtained by polymerization of ethylene oxide and a monodispersed polyethylene glycol obtained by connecting of an oligoethylene glycol having a single molecular weight by a coupling reaction.

In one aspect of the invention, P in formula (1) is a linear polyethylene glycol.

In a preferred embodiment of the aspect, P in formula (1) is represented by formula (2).

$$Y\text{---}(OCH_2CH_2)_n \qquad (2)$$

In the formula, n is the number of repeating units per polyethylene glycol chain, and in the polyethylene glycol having a molecular weight distribution, it is defined that n is calculated by various theoretical calculations based on a number average molecular weight (Mn) of the compound.

In the formula, Y is a hydrocarbon group having from 1 to 24 carbon atoms, specific examples thereof include a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a toicosyl group, a tetracosyl group, a phenyl group, a benzyl group, a cresyl group, a butylphenyl group, a dodecylphenyl group and a trityl group, and Y is preferably a hydrocarbon group having from 1 to 10 carbon atoms, more preferably a methyl group or an ethyl group, and still more preferably a methyl group.

In another preferred embodiment of the aspect, P in formula (1) is represented by formula (3).

$$X^2\text{---}Z^3\text{---}(OCH_2H_2)_n \qquad (3)$$

In the formula, $X^2$ is a chemically reactive functional group different from $X^1$, and $Z^3$ is a divalent spacer between the functional group $X^2$ and the polyethylene glycol chain. Since the polyethylene glycol derivative has two different chemically reactive functional groups $X^1$ and $X^2$, it is possible to provide a polyethylene glycol-drug conjugate having a target-directing property, for example, by connecting a drug to $X^1$ and connecting a target-directing molecule to $X^2$.

Preferred examples of $X^2$ include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group. More specifically, the functional group capable of forming a covalent bond upon a reaction with an amino group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group, an amino group, an oxyamino group or a hydrazide group, the functional group capable of forming a covalent bond upon a reaction with an alkynyl group of the biofunctional molecule is a thiol group or an azide group, and the functional group capable of forming a covalent bond upon a reaction with an azide group of the biofunctional molecule is an alkynyl group.

In a preferred embodiment of the invention, $X^2$ is a group represented by group (I), group (II), group (III), group (IV) or group (V).

Group (I): Functional group capable of forming a covalent bond upon a reaction with an amino group of the biofunctional molecule (a), (b), (c), (d), (e) and (f) shown below:

Group (II): Functional group capable of forming a covalent bond upon a reaction with a thiol group of the biofunctional molecule (a), (b), (c), (d), (e), (f), (g), (h), (i) and (j) shown below:

Group (III): Functional group capable of forming a covalent bond upon a reaction with an aldehyde group or a carboxy group of the biofunctional molecule (g), (k), (l) and (m) shown below:

Group (IV): Functional group capable of forming a covalent bond upon a reaction with an alkynyl group of the biofunctional molecule (g), (k), (l), (m) and (n) shown below:

Group (V): Functional group each capable of forming a covalent bond upon a reaction with an azide group of the biofunctional molecule (j) shown below:

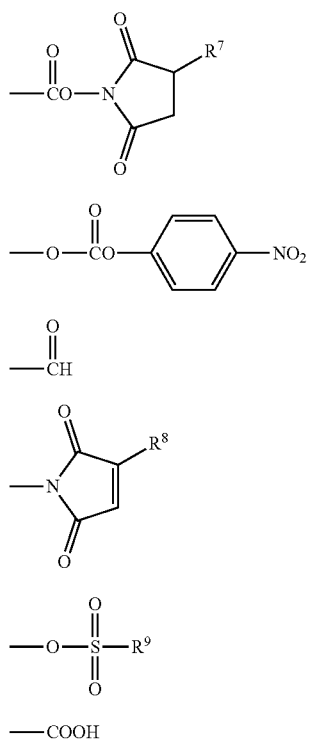

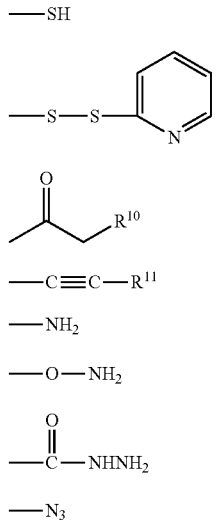

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from a chlorine atom, a bromine atom and an iodine atom.

It is necessary that $X^2$ is different from $X^1$. As to preferred examples of a combination of $X^1$ and $X^2$, when $X^1$ is an active ester group or an active carbonate group, $X^2$ is a group selected from a maleimide group, a vinyl sulfone group, an α-haloacetyl group, an alkynyl group and an azide group; when $X^1$ is an aldehyde group, $X^2$ is a group selected from a maleimide group, a vinyl sulfone group, an alkynyl group and an azide group; when $X^1$ is a maleimide group, a vinyl sulfone group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, a vinyl sulfone group, an α-haloacetyl group, an active ester group, an active carbonate group, an amino group and an oxyamino group; when $X^1$ is an amino group or an oxyamino group, $X^2$ is an alkynyl group, an azide group, a thiol group or a carboxy group; and when $X^1$ is a thiol group, $X^2$ is a group selected from an amino group, an oxyamino group, an azide group and a carboxy group. More preferably, when $X^1$ is an active ester group or an active carbonate group, $X^2$ is a group selected from a maleimide group, an α-haloacetyl group, an alkynyl group and an azide group; when $X^1$ is an aldehyde group, $X^2$ is a group selected from a maleimide group, an α-haloacetyl group, an alkynyl group and an azide group; when $X^1$ is a maleimide group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, an α-haloacetyl group, an active ester group, an active carbonate group, an amino group and an oxyamino group; when $X^1$ is an amino group or an oxyamino group, $X^2$ is an alkynyl group, an azide group or a thiol group; and when $X^1$ is a thiol group, $X^2$ is a group selected from an amino group, an oxyamino group and an azide group.

$Z^3$ is composed of covalent bonds, is not particularly limited as long as it is more stable to acid hydrolysis than the cyclic benzylidene acetal group, and is preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. For example, in the case where it is intended to connect the functional group $X^2$ in a hydrophobic environment, for example, the inside of a protein, p and q are preferably large, and in the case where it is intended to connect it in a hydrophilic environment, p and q are preferably small. However, in the case where $Z^3$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

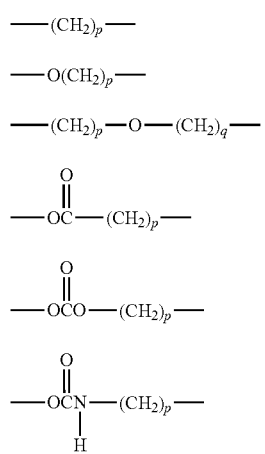

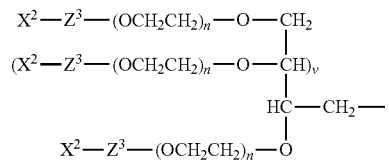

In another aspect of the invention, P in formula (1) is a branched polyethylene glycol.

In a preferred embodiment of the aspect, P in formula (1) is represented by formula (4).

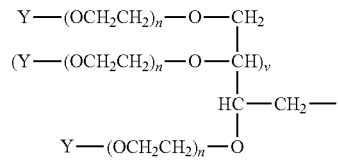

In the formula, Y is a hydrocarbon group having from 1 to 24 carbon atoms as described above, and v is 0 or 2.

In the case where v is 0, two polyethylene glycol chains are present and, in the case where v is 2, four polyethylene glycol chains are present. In general, in the chemical modification of a bio-related substance with polyethylene glycol, when connecting points to the polyethylene glycol are introduced more than necessary, the active sites of the bio-related substance are destroyed to reduce its function so that an attempt to increase the effect by increasing a molecular weight of the polyethylene glycol has been performed. However, the viscosity increases with the increase in the molecular weight and hence, for example, handling as an aqueous solution preparation, for example, an injection preparation becomes difficult. Since the polyethylene glycol derivative has a branched structure, it shows low viscosity in comparison with a linear polyethylene glycol derivative having the same molecular weight, and thus it is useful in application, for example, the aqueous solution preparation.

In another preferred embodiment of the aspect, P in formula (1) is represented by formula (5).

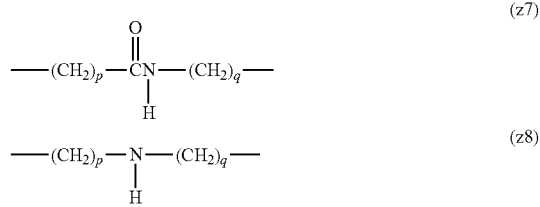

In the formula, $X^2$ is a chemically reactive functional group different from $X^1$ as described above, $Z^3$ is a divalent spacer as described above, and v is 0 or 2.

The polyethylene glycol derivative has one $X^1$ and two or four $X^2$ and, for example, when a drug is connected to $X^1$ and a target-directing molecule is connected to $X^2$, high target-directing performance can be obtained.

In still another preferred embodiment of the aspect, P in formula (1) is represented by formula (6).

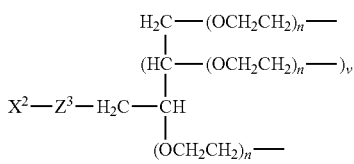
(6)

In the formula, $X^2$ is a chemically reactive functional group different from $X^1$ as described above, $Z^3$ is a divalent spacer as described above, and v is 0 or 2.

In the antibody-drug conjugate (ADC)-related field, in order to increase drug transportation efficiency, it is preferred to connect a plurality of drugs to an antibody, but when a plurality of connecting points are introduced into the antibody, a problem arises in that the affinity to an antigen is decreased. The polyethylene glycol derivative has two or four $X^1$ and one $X^2$, and, for example, when an anticancer agent is connected to $X^1$ and an antibody is connected to $X^2$ in ADC targeting cancer, it is possible to improve the transportation efficiency of the anticancer agent without increasing the connecting points to the antibody.

In still another aspect of the invention, P in formula (1) is polyethylene glycol having the number of terminals of 2 to 8, all the terminals of the polyethylene glycol constituting P are each connected to $Z^1$, and w is equal to the number of terminals of the polyethylene glycol.

In a preferred embodiment of the aspect, P in formula (1) is selected from the group consisting of formula (r), formula (s), formula (t), formula (u) and formula (v). w is 2 in the case where P is represented by formula (r), w is 3 in the case where P is represented by formula (s), w is 4 in the case where P is represented by formula (t), w is 4 in the case where P is represented by formula (u), and w is 8 in the case where P is represented by formula (v).

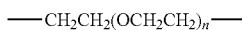
(r)

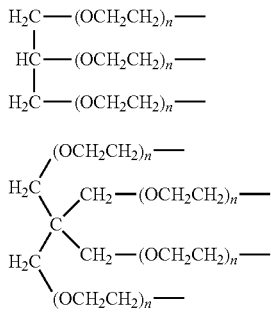
(s)

(t)

(u)

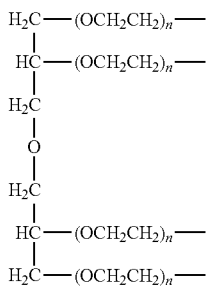

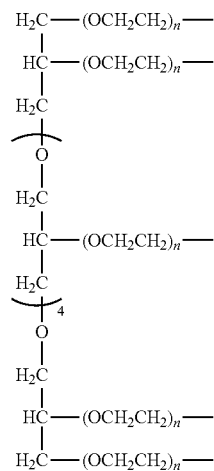
(v)

A preferred range of n in formula (2) and formula (3) of the invention is from 3 to 2,000, more preferably from 20 to 1,500, still more preferably from 40 to 1,000, and most preferably from 60 to 500. Further, a preferred range of n in formula (4), formula (5) and formula (6) is from 3 to 1,000, preferably from 10 to 800, more preferably from 20 to 500, and most preferably from 30 to 300.

According to another aspect of the invention, a cyclic benzylidene acetal linker compound represented by formula (55) is provided.

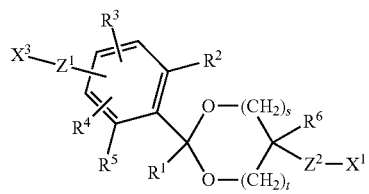
(55)

Each of $R^1$ and $R^6$ in formula (55) of the invention is a hydrogen atom or a hydrocarbon group, a number of carbon atoms of the hydrocarbon group is preferably 10 or less and specific examples of the hydrocarbon group include a methyl group, an ethyl group, a propyl group, an isopropyl group, a tert-butyl group, a phenyl group and a benzyl group. A preferred embodiment of $R^1$ is a hydrogen atom or a methyl group, and a hydrogen atom is more preferred.

The benzene ring in formula (55) of the invention may have a plurality of substituents. By appropriately selecting the kind, the position and the degree of electron-donating property and electron-withdrawing property of the substituents on the benzene ring, it is possible to adjust the degrees of electron density and steric hindrance around the acetal group which affects the hydrolysis rate of the cyclic acetal linker. This makes it possible to impart a desired hydrolysis rate to the cyclic acetal linker.

In the specification, the substituent(s) on the benzene ring in formula (55) is described using the "substituent constant (a)" which means the substituent constant in the Hammett's rule which quantifies the effect of the substituent on the reaction rate or equilibrium of benzene derivative. However, as is known, the Hammett's rule is applied only to a para-substituted or meta-substituted benzene derivative and cannot be applied to an ortho-substituted benzene derivative which is affected by steric hindrance. Therefore, in the case of ortho-substituted benzene derivative, the substituent constant means the substituent constant in the Taft's equation which extends the Hammett's rule described above.

As is known, since the reaction constant (ρ) of para-substituted or meta-substituted benzene derivative in the Hammett's rule and the reaction constant (ρ*) of ortho-substituted benzene derivative in the Taft's equation are approximately equal, it is defined in the specification that ρ and ρ* are the same. Since the substituent constant (σ*) in the ortho position in the Taft's equation is similar to the substituent constant in the para position as described, for example, in "Charton, M. Can. J. Chem. 1960, 38, 2493-2499", to the substituent constant in the ortho position in the specification is applied a corresponding substituent constant in the para position.

The substituent constant (σ) in the para position or the meta position is described in "Hansch, C.; Leo, A.; Taft, R. W. Chem. Rev. 1991, 91, 165-195", and with respect to a substituent in which the substituent constant (σ) is unknown the constant can be measured and determined by the method described in "Hammett, L. P. Chem. Rev. 1935, 17(1), 125-136". Moreover, the position constant (Es) in the Taft's equation is described in "Unger, S. H.; Hansch, C. Prog. Phys. Org. Chem. 1976, 12, 91-118". However, as to Es as used in the specification, a hydrogen atom is defined as "0".

In formula (55), in the case where a plurality of substituents are present on the benzene ring, it is defined that additivity is established for the substituent constant (σ) and the position constant (Es) thereof, and the sum of σ is represented by "Σσ" and the sum of Es is represented by "ΣEs".

$Z^1$ is connected to the benzene ring of the cyclic benzylidene acetal and $X^3$—$Z^1$ is also a substituent of the benzene ring. The substituent constant of $X^3$—$Z^1$ can be determined by separately measuring the combination of $X^3$ and $Z^1$, but, since the substituent constant of $X^3$—$Z^1$ is substantially affected largely by the structure in the vicinity of the connecting portion to the benzene ring, the effect of the other portions is so small as to be ignored. Therefore, it is possible to use a known substituent constant of a structure similar to the structure in the vicinity of the connecting portion to the benzene ring in place of separately measuring the substituent constant as to $X^3$—$Z^1$.

It is defined that the substituent constant of $X^3$—$Z^1$ in the specification can be substituted with a substituent constant of a structure in which atom(s) connected to the third atom counted from the atom connected to the benzene atom of the backbone atoms of the main chain of $X^3$—$Z^1$, excepting the second atom are substituted with hydrogen atom(s). However, in the case where, when the atom is substituted with a hydrogen atom, a carboxy group is formed, it is defined that the substituent constant of $X^3$—$Z^1$ can be substituted with a substituent constant of a structure in which the atom is substituted with a methyl group in place of a hydrogen atom. Moreover, in the case where the backbone atoms of the main chain of $X^3$—$Z^1$ is 4 atoms or less, a known substitution constant described in the references described above is used or a value obtained by measuring according to the method described in the references described above can be used.

Specific examples of the structure of the connecting portion to the benzene ring in $X^3$—$Z^1$ and the structure for the substitution are shown below. In the case of (r1) shown below, wherein the connecting portion to the benzene ring in $X^3$—$Z^1$ is an ether bond, a substituent constant of (r2) shown below is applied. In the cases of (r3) and (r5) shown below, wherein the connecting portion to the benzene ring in $X^3$—$Z^1$ is an amide bond, substituent constants of (r4) and (r6) shown below are applied, respectively. In the case of (r7) shown below, wherein the connecting portion to the benzene ring in $X^3$—$Z^1$ is a urethane bond, a substituent constant of (r8) shown below is applied.

| | Structure of Connecting Portion to Benzene Ring | | Structure for Substitution |
|---|---|---|---|
| (r1) | —CH$_2$CH$_2$O—⌬ | (r2) | H—CH$_2$CH$_2$O—⌬ |
| (r3) | —CH$_2$C(=O)N(H)—⌬ | (r4) | H—CH$_2$C(=O)N(H)—⌬ |
| (r5) | —CH$_2$N(H)C(=O)—⌬ | (r6) | H—CH$_2$N(H)C(=O)—⌬ |
| (r7) | —OC(=O)N(H)—⌬ | (r8) | CH$_3$—OC(=O)N(H)—⌬ |

The substituent which can be used in the aspect is a substituent which does not inhibit the acetalization reaction and the terminal functional group conversion reaction in the synthesis process of the cyclic benzylidene acetal linker compound, and in a preferred embodiment of the invention it is a substituent which does not inhibit the coupling reaction of the linker compound with the hydrophilic polymer intermediate, the terminal functional group conversion reaction of the hydrophilic polymer derivative obtained and the bond-forming reaction between the hydrophilic polymer derivative and the drug or the like, in addition to the reactions described above.

The substituent may be any of electron-withdrawing substituent and electron-donating substituent as far as it satisfies the conditions described above, and the substituents may be used individually or in combination. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para-position and ortho-position includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

As to the hydrolysis rate of the cyclic benzylidene acetal linker compound of the invention, hydrolysis half-life ($t_{1/2}$) in a buffer at pH 5.5 and 37° C. is preferably in the range from 1 hour to 6 months, more preferably in the range from 1 hour to 1 month, and still more preferably in the range from 1 hour to 24 hours.

In the case where formula (55) includes a 1,3-dioxolane structure and $R^2$ and $R^5$ are hydrogen atoms, a preferred range of sum ($\Sigma\sigma$) of substituent constants satisfies $-0.30 \leq \Sigma\sigma \leq 0.21$ at the time of 1 hour $\leq t_{1/2} \leq 24$ hours, $-0.30 \leq \Sigma\sigma \leq 0.76$ at the time of 1 hour $\leq t_{1/2} \leq 1$ month and $-0.30 \leq \Sigma\sigma \leq 1.05$ at the time of 1 hour $\leq t_{1/2}$ 6 months.

In the case where formula (55) includes a 1,3-dioxolane structure and at least one of $R^2$ and $R^5$ is a substituent other than a hydrogen atom, the range of $\Sigma\sigma$ satisfies $-1.71 \leq \Sigma\sigma \leq 0.04$ at the time of 1 hour $\leq t_{1/2} \leq 24$ hours, $-1.71 \leq \Sigma\sigma \leq 0.59$ at the time of 1 hour $\leq t_{1/2} \leq 1$ month and $-1.71 \leq \Sigma\sigma \leq 0.88$ at the time of 1 hour $\leq t_{1/2} \leq 6$ months.

In the case where formula (55) includes a 1,3-dioxolane structure and $R^2$ and $R^5$ are hydrogen atoms, for example, a preferred embodiment which satisfies $-0.30 \leq \Sigma\sigma \leq 0.21$ at the time of 1 hour $\leq t_{1/2} \leq 24$ hours is described below. However, the substituents shown herein means $R^3$, $R^4$ and $X^3$—$Z^1$ and the structure used in place of $X^3$—$Z^1$ according to the definition described above. In the preferred embodiment, one of the meta-positions in formula (55) is a methoxy group, an ethoxy group or an acetamide group, and more preferably an ethoxy group or an acetamide group. In another preferred embodiment, the para-position in formula (55) is a methoxy group or an ethoxy group and one of the meta-positions is a substituent selected from the group consisting of a fluorine atom, a chlorine atom, a bromine atom and an iodine atom, and more preferably the para-position is an ethoxy group and one of the meta-positions is a fluorine atom or a chlorine atom. In still another preferred embodiment, one of the para-position and the meta-position in formula (55) is a methoxy group, an ethoxy group or an acetamide group, and more preferably a methoxy group or an ethoxy group.

Further, in the case where formula (55) includes a 1,3-dioxolane structure and at least one of $R^2$ and $R^5$ is a substituent other than a hydrogen atom, for example, a preferred embodiment which satisfies $-1.71 \leq \Sigma\sigma \leq 0.04$ at the time of 1 hour $\leq t_{1/2} \leq 24$ hours is described below. However, the substituents shown herein means $R^3$, $R^4$ and $X^3$—$Z^1$ and the structure used in place of $X^3$—$Z^1$ according to the definition described above. In the case where one of $R^2$ and $R^5$ in formula (55) is a fluorine atom, a methyl group or an ethyl group and the other is a hydrogen atom, the para-position is preferably an ethoxy group or an acetamide group, and more preferably an ethoxy group. In the case where one of $R^2$ and $R^5$ in formula (55) is a methoxy group and the other is a hydrogen atom, the para-position is preferably a substituent selected from the group consisting of a methoxymethyl group and an acetamide group, and more preferably an acetamide group.

In the case where formula (55) includes a 1,3-dioxane structure and $R^2$ and $R^5$ are hydrogen atoms, a preferred range of sum ($\Sigma\sigma$) of substituent constants satisfies $-0.19 \leq \Sigma\sigma \leq 0.10$ at the time of 1 hour $\leq t_{1/2} \leq 24$ hours, $-0.19 \leq \Sigma\sigma \leq 0.41$ at the time of 1 hour $\leq t_{1/2} \leq 1$ month and $-0.19 \leq \Sigma\sigma \leq 0.57$ at the time of 1 hour $\leq t_{1/2} \leq 6$ months.

Further, in the case where formula (55) includes a 1,3-dioxane structure and at least one of $R^2$ and $R^5$ is a substituent other than a hydrogen atom, the range of $\Sigma\sigma$ satisfies $-0.98 \leq \Sigma\sigma \leq 0.00$ at the time of 1 hour $\leq t_{1/2} \leq 24$ hours, $-0.98 \leq \Sigma\sigma \leq 0.31$ at the time of 1 hour $\leq t_{1/2} \leq 1$ month and $-0.98 \leq \Sigma\sigma \leq 0.48$ at the time of 1 hour $\leq t_{1/2} \leq 6$ months.

$X^3$ and $X^4$ in formula (55) are each independently a chemically reactive functional group, and although it is not intended to limit the application of the linker compound, in a preferred embodiment of the invention, the hydrophilic polymer derivative having a cyclic benzylidene acetal linker of formula (1) can be synthesized by a coupling reaction between $X^3$ and a chemically reactive functional group of a hydrophilic polymer intermediate.

Preferred examples of $X^3$ and $X^4$ in formula (55) include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group, an azide group and a hydroxy group. According to a more specific embodiment, the functional group capable of forming a covalent bond upon a reaction with an amino group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group or a carboxy group; the functional group capable of forming a covalent bond upon a reaction with a thiol group of the reaction partner is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group; the functional group capable of forming a covalent bond upon a reaction with an aldehyde group or a carboxy group of the reaction partner is a thiol group, an amino group, an oxyamino group or a hydrazide group; the functional group capable of forming a covalent bond upon a reaction with an alkynyl group of the reaction partner is a thiol group or an azide group; the functional group capable of forming a covalent bond upon a reaction with an azide group of the reaction partner is an alkynyl group; and the functional group capable of forming a covalent bond upon a reaction with a halogenated alkyl group, an alkylsulfonate or an arylsulfonate of the reaction partner is a hydroxy group, a thiol group or an amino group.

In a preferred embodiment of the aspect, $X^3$ and $X^4$ are each a group represented by group (I), group (II), group (III), group (IV), group (V) or group (VI).

Group (I): Functional group capable of forming a covalent bond upon a reaction with an amino group of the reaction partner (a), (b), (c), (d), (e) and (f) shown below:

Group (II): Functional group capable of forming a covalent bond upon a reaction with a thiol group of the reaction partner (a), (b), (c), (d), (e), (f), (g), (h), (i) and (j) shown below:

Group (III): Functional group capable of forming a covalent bond upon a reaction with an aldehyde group or a carboxy group of the reaction partner (g), (k), (l) and (m) shown below:

Group (IV): Functional group capable of forming a covalent bond upon a reaction with an alkynyl group of the reaction partner (g), (k), (l), (m) and (n) shown below:

Group (V): Functional group capable of forming a covalent bond upon a reaction with an azide group of the reaction partner (j) shown below:

Group (VI): Functional group capable of forming a covalent bond upon a reaction with a halogenated alkyl group, an alkylsulfonate or an arylsulfonate of the reaction partner (o), (g) and (k) shown below:

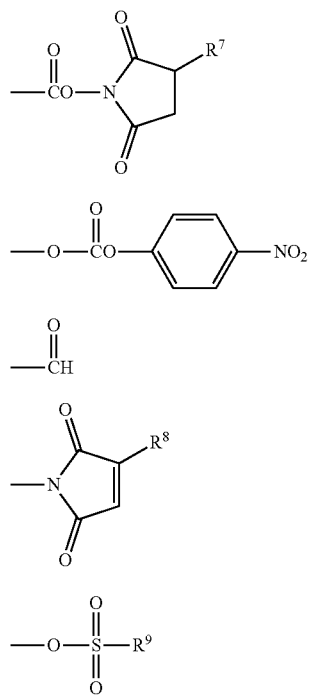

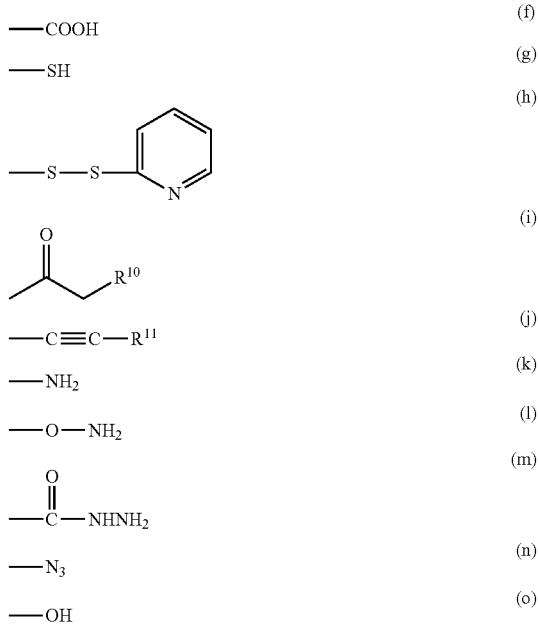

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from a chlorine atom, a bromine atom and an iodine atom.

$X^3$ and $X^4$ may be the same or different from each other. As to preferred examples of a combination of $X^3$ and $X^4$ which are different from each other, when $X^3$ is an active ester group or an active carbonate group, $X^4$ is a group selected from a maleimide group, a vinyl sulfone group, an α-haloacetyl group, an alkynyl group and an azide group; when $X^3$ is an aldehyde group, $X^4$ is a group selected from a maleimide group, a vinyl sulfone group, an alkynyl group and an azide group; when $X^3$ is a maleimide group, a vinyl sulfone group or an α-haloacetyl group, $X^4$ is a group selected from an active ester group, an active carbonate group, an alkynyl group and an azide group; when $X^3$ is an alkynyl group or an azide group, $X^4$ is a group selected from a maleimide group, a vinyl sulfone group, an α-haloacetyl group, an active ester group, an active carbonate group, an amino group, an oxyamino group and a hydroxy group; when $X^3$ is an amino group or an oxyamino group, $X^4$ is an alkynyl group, an azide group, a thiol group, a hydroxy group or a carboxy group; and when $X^3$ is a thiol group or a hydroxy group, $X^4$ is a group selected from an amino group, an oxyamino group, an azide group and a carboxy group. More preferably, when $X^3$ is an active ester or an active carbonate group, $X^4$ is a group selected from a maleimide group, an α-haloacetyl group, an alkynyl group and an azide group; when $X^3$ is an aldehyde group, $X^4$ is a group selected from a maleimide group, an α-haloacetyl group, an alkynyl group and an azide group; when $X^3$ is a maleimide group or an α-haloacetyl group, $X^4$ is a group selected from an active ester group, an active carbonate group, an alkynyl group and an azide group; when $X^3$ is an alkynyl group or an azide group, $X^4$ is a group selected from a maleimide group, an α-haloacetyl group, an active ester group, an active carbonate group, an amino group, an oxyamino group and a hydroxy group; when $X^3$ is an amino group or an oxyamino group, $X^4$ is an alkynyl group, an azide group, a hydroxy group or a thiol group; and when $X^3$ is a thiol group or a hydroxy group, $X^4$ is a group selected from an amino group, an oxyamino group and an azide group.

$Z^1$ in formula (55) of the aspect is a divalent spacer between the benzene ring of the cyclic benzylidene acetal group and the functional group $X^3$, and $Z^2$ is a divalent spacer between the functional group $X^4$ and the cyclic benzylidene acetal group. These are composed of covalent bonds, are not particularly limited as long as they are more stable to acid hydrolysis than the cyclic benzylidene acetal group, and are preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. However, in the case where at least one of $Z^1$ and $Z^2$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

 (z1)

 (z2)

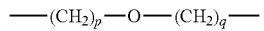 (z3)

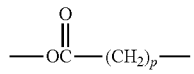 (z4)

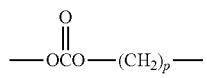 (z5)

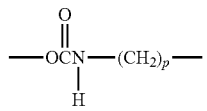 (z6)

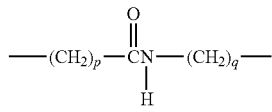 (z7)

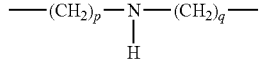 (z8)

The hydrophilic polymer derivative having a cyclic benzylidene acetal linker of the invention can be synthesized by performing a coupling reaction between a cyclic benzylidene acetal linker compound having a substituent and a hydrophilic polymer intermediate. The bond generated by the coupling reaction is determined by a combination of the functional groups used in the reaction, and is the ether bond, the ester bond, the carbonate bond, the urethane bond, the amide bond, the secondary amino group, the alkylene group containing any of these bonds and group, the single bond or the alkylene group contained in the divalent spacer $Z^1$ described above. In the hydrophilic polymer derivative synthesized, the terminal functional group is chemically converted, if desired. As the reaction used for the functional group conversion, a conventionally known method can be used, but it is necessary to appropriately select conditions which do not decompose the cyclic benzylidene acetal group of formula (1) and the bonds contained in the divalent spacers $Z^1$ and $Z^2$ described above.

As a typical example of performing the coupling reaction between the cyclic benzylidene acetal linker compound and the hydrophilic polymer intermediate and further the chemical conversion of the terminal functional group, the steps described below are exemplified. Polyethylene glycol which is a typical hydrophilic polymer is described herein as an example.

(A) Synthesis of cyclic benzylidene acetal linker compound

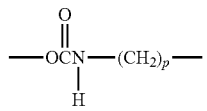

(14)

wherein $R^1$ is a hydrogen atom or a hydrocarbon group; and $R^2$, $R^3$, $R^4$ and $R^5$ are each independently an electron-withdrawing or electron-donating substituent or a hydrogen atom.

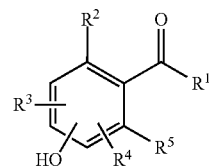

(15)

A carbonyl compound of formula (14) having a hydroxy group which is a chemically reactive functional group is allowed to react with a 1,2-diol derivative of formula (15) having a phthalimide group in which an amino group is protected with a phthaloyl group in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an acid catalyst to obtain a compound of the following formula (16) having a cyclic benzylidene acetal group. The resulting compound may be purified by extraction, recrystallization, adsorbent treatment, column chromatography or the like. In place of the carbonyl compound, it is possible to use a corresponding acetal derivative of a lower alcohol. The lower alcohol is preferably an alcohol having from 1 to 5 carbon atoms, and more preferably methanol or ethanol. The acid catalyst may be either an organic acid or an inorganic acid and is not particularly limited, and specific examples thereof include p-toluenesulfonic acid, pyridinium p-toluenesulfonate, methanesulfonic acid, 10-camphorsulfonic acid, hydrogen chloride, iodine, ammonium chloride, oxalic acid, boron trifluoride-diethyl ether complex and the like.

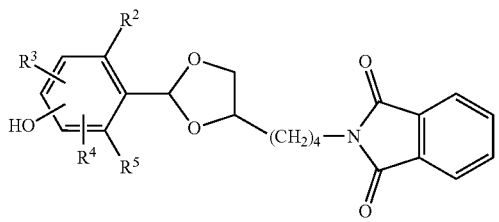

(16)

The "protective group" as referred to herein is a component which prevents or blocks a reaction of a specific chemically reactive functional group in a molecule under certain reaction conditions. The protective group varies depending on the kind of the chemically reactive functional group to be protected, the conditions to be used and the presence of the other functional group or protective group in the molecule. Specific examples of the protective group can be found in many general books and are described, for example, in "Wuts, P. G. M.; Greene, T. W., Protective Groups in Organic Synthesis, 4th ed.; Wiley-Interscience: New York, 2007". Moreover, the functional group protected by the protective group can be reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the literature described above.

As the chemically reactive functional group in the compound of formula (14), a functional group other than the hydroxy group can also be used. Specific examples thereof include a hydroxyalkyl group, an amino group, an aminoalkyl group, a carboxy group and a carboxyalkyl group. Also, the functional group described above may be protected by a protective group which is stable in the acidic conditions of the acetalization reaction and can be deprotected under reaction conditions other than catalytic reduction by which the cyclic benzylidene acetal group is decomposed. As to preferred combinations of the functional group to be protected and the protective group, when the functional group to be protected is a hydroxy group or a hydroxyalkyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is an amino group or an aminoalkyl group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a carboxy group or a carboxyalkyl group, for example, an alkyl ester protective group and a silyl ester protective group are exemplified, and specific examples thereof include a methyl group, a 9-fluorenylmethyl group and a tert-butyldimethylsilyl group. The kinds and the typical deprotection conditions of the specific protective groups are described in the literature described above, and the reaction conditions suitable for each of the protective groups are selected and the deprotection can be performed before the reaction with the hydrophilic polymer intermediate.

Moreover, as the chemically reactive functional group excepting the 1,2-diol moiety in the compound of formula (15), a functional group other than the phthalimide group can also be used. In the case where the chemically reactive functional group is a functional group which is protected by a protective group, it is necessary that the protective group is stable in the acidic conditions of the acetalization reaction and can be deprotected under reaction conditions other than catalytic reduction by which the benzylidene acetal group is decomposed. As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinotrophenyl group, an S-9-fluorenylmethyloxycarbonyl group and an S-tert-butyldisulfide group. The typical deprotection conditions of the protective group are described in the literature described above, and the reaction conditions suitable for each of the protective groups are selected. However, in the case where the chemically reactive functional group is a functional group which does not inhibit the acetalization reaction even when it is not protected by a protective group, it is not necessary to use a protective group.

(B) Synthesis of Polyethylene Glycol Intermediate

Ethylene oxide is polymerized in an amount of 3 to 2,000 molar equivalents to methanol, which is an initiator, in toluene or with no solvent under alkaline conditions, for example, metallic sodium, metallic potassium, sodium hydride or potassium hydride to obtain polyethylene glycol of formula (17). The initiator is preferably an alcohol having a hydrocarbon group having from 1 to 24 carbon atoms, and specifically includes methanol, ethanol, propanol, isopropanol, butanol, tert-butanol, phenol and benzyl alcohol. Since the polyethylene glycol has a hydroxy group which is a chemically reactive functional group, it can be used as it is in a coupling reaction with a cyclic benzylidene acetal linker compound.

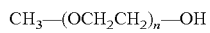
(17)

The polyethylene glycol of formula (17) is allowed to react with methanesulfonyl chloride in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a polyethylene glycol intermediate of formula (18). The organic base and inorganic base may not be used. The use ratio of the organic base or the inorganic base is not particularly limited, and is preferably equimolar or more to the hydroxyl group of the polyethylene glycol of formula (17). Also, it is possible to use the organic base as a solvent. The compound obtained may be purified by a purification means, for example, extraction, recrystallization, adsorbent treatment, reprecipitation, column chromatography or supercritical extraction.

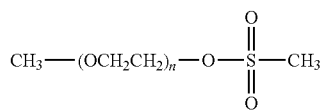
(18)

As the chemically reactive functional group in the polyethylene glycol intermediate of formula (18), other functional groups can be also used. Preferred examples of the chemically reactive functional group are functional groups wherein the bond generated by the coupling reaction of the polyethylene glycol intermediate with the cyclic benzylidene acetal linker compound described above becomes the ether bond, the ester bond, the carbonate bond, the urethane bond, the amide bond, the secondary amino group, the alkylene group containing any of these bonds and group, the single bond or the alkylene group contained in the divalent spacer $Z^1$ of formula (1), and specifically include, for example, a halogen atom, an active ester, an active carbonate, an aldehyde group, an amino group, a hydroxy group and a carboxy group.

(C) Coupling Reaction Between Cyclic Benzylidene Acetal Linker Compound and Polyethylene Glycol Intermediate The benzylidene acetal linker compound of formula (16) and the polyethylene glycol intermediate of formula (18) are subjected to a coupling reaction in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, potassium tert-butoxide or sodium hexamethyldisilazane or an inorganic base, for example, potassium carbonate, potassium hydroxide or sodium hydride to obtain a compound of formula (19). The use ratio of the organic base or the inorganic base is not particularly limited, and is preferably equimolar or more to the chemically reactive functional group of the polyethylene glycol intermediate of formula (18). Also, it is possible to use the organic base as a solvent. The compound obtained may be purified by the purification means described above.

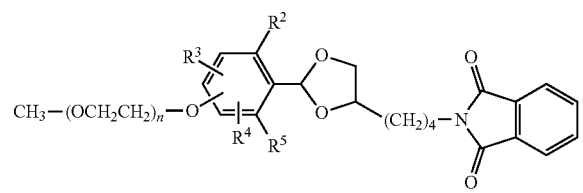
(19)

The chemically reactive functional group of the cyclic benzylidene acetal linker compound may be subjected to functional group conversion before the coupling reaction with the polyethylene glycol intermediate. The reaction conditions for the coupling reaction are determined depending on the combination of the chemically reactive functional group of the cyclic benzylidene acetal linker compound and the chemically reactive functional group of the polyethylene glycol intermediate and a conventionally known method can be used. However, it is necessary to appropriately select conditions which do not decompose the bonds contained in the cyclic benzylidene acetal group and the divalent spacers $Z^1$ and $Z^2$ described above of formula (1)

(D) Terminal Functional Group Conversion of the Polyethylene Glycol Derivative Having Cyclic Benzylidene Acetal Linker The compound of formula (19) is treated by using a basic organic compound, for example, ethylenediamine, methyl hydrazine or methylamine or a basic inorganic compound, for example, hydrazine, hydroxylamine or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (20) in which the phthalimide group is deprotected and converted into an amino group. The use ratio of the basic compound is not particularly limited, and is preferably equimolar or more to the chemically reactive functional group of the compound of formula (19). Also, it is possible to use the basic compound as a solvent. The compound obtained may be purified by the purification means described above.

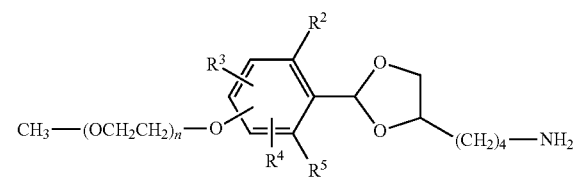
(20)

Furthermore, the compound of formula (20) is allowed to react with N-succinimidyl 3-maleimidopropionate in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (21) in which a maleimide group is introduced into the terminal. The organic base and inorganic base may not be used. The use ratio of the organic base or the inorganic base is not particularly limited, and is preferably equimolar or more to the chemically reactive functional group of the compound of formula (20). Also, it is possible to use the organic base as a solvent. The compound obtained may be purified by the purification means described above.

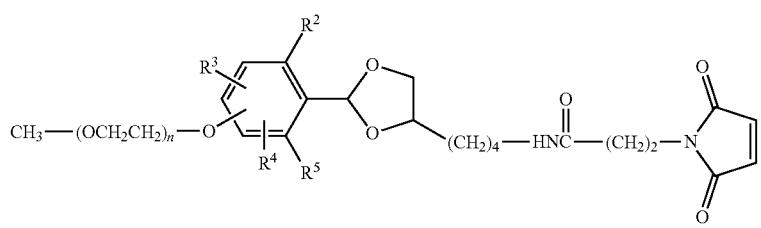

(21)

EXAMPLES

The invention will be described more specifically with reference to the examples, but the invention should not be construed as being limited thereto.

In $^1$H-NMR analysis, JNM-ECP400 or JNM-ECA600 produced by JEOL DATUM Ltd. was used. For the measurement, a tube of 5 mm ϕ was used, and tetramethylsilane (TMS) was used as an internal standard substance in the case where a deuterated solvent was $CDCl_3$, $CD_3CN$ or $CD_3OD$, or HDO was used as a standard in the case of $D_2O$.

In gel permeation chromatography (GPC) analysis, there were used SHODEX GPC SYSTEM-11 as a GPC system, SHODEX RIX8 as a differential refractometer which is a detector, and three columns, i.e., SHODEX KF801L, KF803L and KF804L (ϕ 8 mm×300 mm) connected in series as GPC columns, and the temperature of the column oven was set to 40° C. The measurement was performed using tetrahydrofuran as an eluent, at the flow rate of 1 ml/min, at the sample concentration of 0.1% by weight, and in the injection volume of 0.1 ml. The calibration curves prepared by using ethylene glycol, diethylene glycol and triethylene glycol produced by Kanto Chemical Co., Ltd. and Polymer Standards for GPC of polyethylene glycol or polyethylene oxide having a molecular weight of 600 to 70,000 produced by Polymer Laboratory Co., Ltd. For analysis of data, BORWIN GPC calculation program was used. Mn represents a number average molecular weight, Mw represents a weight average molecular weight, and a molecular weight distribution is indicated as a calculated value of Mw/Mn.

A deuterated water buffer of MES (2-morpholinoethanesulfonic acid) having pD of 5.5 and a deuterated water buffer of HEPES (2-[4-(Hydroxyethyl)-1-piperazinyl]ethanesulfonic acid) having pD of 7.4 for use in hydrolysis test were prepared by adding a 0.1M sodium hydroxide deuterated water solution to a 0.1M MES deuterated water solution and a 0.1M HEPES deuterated water solution, respectively, based on the relational equation shown below described in "Glasoe, P. K.; Long, F. A., J. Phys. Chem. 1960, 64, 188-190".

pD=Measured value by pH meter+0.40

A hydrolysis ratio was evaluated by $^1$H-NMR and calculated according to the calculation equation shown below by taking an integrated value of the hydrogen of the acetal group and an integral value of the hydrogen of the aldehyde group to be formed by hydrolysis as $I^1$ and $I^2$, respectively.

Hydrolysis ratio (%)=[$I^2$/($I^1$+$I^2$)]×100

Example 1

Into a 200 mL three-necked flask equipped with a thermometer, a nitrogen inlet tube, a stirrer, a Dean-stark tube and a condenser tube were charged 1,2,6-hexanetriol (30.0 g, 0.224 mol), acetone dimethyl acetal (25.6 g, 0.246 mol) and p-toluenesulfonic acid monohydrate (0.426 g, 2.24 mmol), and the reaction was performed at 80° C. for 3 hours while distilling off methanol. Triethylamine (0.453 g, 4.48 mmol) was added thereto and the mixture was stirred for a while, diluted with ethyl acetate, and washed with an aqueous 20% by weight sodium chloride solution. The organic layer was dried over anhydrous sodium sulfate, and after filtration, the solvent was distilled off under a reduced pressure. The residue was purified by silica gel chromatography to obtain a compound of formula (22).

$^1$H-NMR (CDCl$_3$, internal standard TMS); δ (ppm):
1.35 (3H, s, —C$\underline{H}_3$), 1.41 (3H, s, —C$\underline{H}_3$), 1.49-1.67 (6H, m, >CHC$\underline{H}_2$C$\underline{H}_2$C$\underline{H}_2$—), 2.07 (1H, brs, —O$\underline{H}$), 3.51 (1H, t, —OC$\underline{H}_2$CH<), 3.64 (2H, t, —C$\underline{H}_2$OH), 4.04 (1H, dd, —OCH$_2$CH<), 4.07-4.10 (1H, m, —OCH$_2$C$\underline{H}$<)

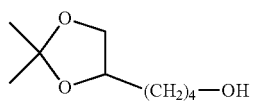

(22)

Example 2

Into a 500 mL four-necked flask equipped with a thermometer, a nitrogen inlet tube, a stirrer and a condenser tube were charged the compound of formula (22) (20.0 g, 0.115 mol), triethylamine (23.3 g, 0.230 mol) and toluene (200 g) and the mixture was cooled to 10° C. or less. While continuing the cooling, methanesulfonyl chloride (19.8 g, 0.173 mol) prepared in a dropping funnel was gradually added dropwise thereto. After the completion of the dropwise addition, the reaction was performed at 20° C. for 2 hours. Ethanol (7.97 g, 0.173 mol) was added and the mixture was stirred for a while and filtered. The organic layer was washed with ion-exchanged water, dried over anhydrous sodium sulfate, and after filtration, the solvent was distilled off under a reduced pressure to obtain a compound of formula (23).

$^1$H-NMR (CDCl$_3$, internal standard TMS); δ (ppm):
1.35 (3H, s, —C$\underline{H}_3$), 1.40 (3H, s, —C$\underline{H}_3$), 1.44-1.83 (6H, m, >CHC$\underline{H}_2$C$\underline{H}_2$C$\underline{H}_2$—), 3.01 (3H, s, —OSO$_2$C$\underline{H}_3$), 3.51 (1H, t, —OC$\underline{H}_2$CH<), 4.03-4.11 (2H, m, —OC$\underline{H}_2$CH<, —OCH$_2$C$\underline{H}$<), 4.24 (2H, t, —C$\underline{H}_2$OSO$_2$CH$_3$)

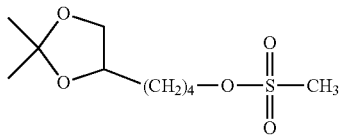

(23)

Example 3

Into a 500 mL four-necked flask equipped with a thermometer, a nitrogen inlet tube, a stirrer and a condenser tube were charged the compound of formula (23) (20.0 g, 79.3 mmol), potassium phthalimide (17.6 g, 95.2 mmol) and dehydrated dimethylformamide (200 g), and the reaction was performed at 60° C. for 2 hours. The mixture was cooled to 10° C. or less, ion-exchanged water (400 g) was added thereto and after stirring for a while, the mixture was extracted with a mixed solution of ethyl acetate/hexane (60/40 in v/v). The organic layer was washed with an aqueous 0.2% by weight potassium carbonate solution and dried over anhydrous sodium sulfate. After filtration, the solvent was distilled off under a reduced pressure to obtain a compound of formula (24).

$^1$H-NMR (CDCl$_3$, internal standard TMS); δ (ppm):
1.34 (3H, s, —C$\underline{H}_3$), 1.39 (3H, s, —C$\underline{H}_3$), 1.44-1.75 (6H, m, >CHC$\underline{H}_2$C$\underline{H}_2$C$\underline{H}_2$—), 3.50 (1H, t, —OC$\underline{H}_2$CH<), 3.69 (2H, t, —C$\underline{H}_2$-phthalimide), 4.01-4.09 (2H, m, —OC$\underline{H}_2$CH<, —OCH$_2$C$\underline{H}$<), 7.71-7.85 (4H, m, -phthalimide)

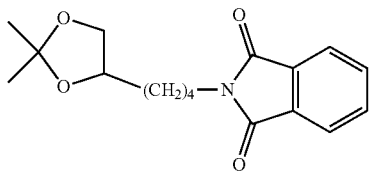

(24)

Example 4

Into a 1 L four-necked flask equipped with a thermometer, a nitrogen inlet tube, a stirrer and a condenser tube were charged the compound of formula (24) (15.2 g, 50.0 mmol), p-toluenesulfonic acid monohydrate (951 mg, 5.00 mmol) and methanol (500 mL), and the reaction was performed at room temperature for 4 hours. Triethylamine (1.01 g, 10.0 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (25).

$^1$H-NMR (CD$_3$CN, internal standard TMS); δ (ppm):
1.24-1.61 (6H, m, >CHC$\underline{H}_2$C$\underline{H}_2$C$\underline{H}_2$—), 2.69 (1H, t, —O$\underline{H}$), 2.75 (1H, d, —O$\underline{H}$), 3.17-3.21 (1H, m, —OC$\underline{H}_2$CH<), 3.31-3.37 (1H, m, —OC$\underline{H}_2$CH<), 3.39-3.43 (1H, m, —OCH$_2$C$\underline{H}$<), 3.54 (2H, t, —C$\underline{H}_2$-phthalimide), 7.67-7.75 (4H, m, -phthalimide)

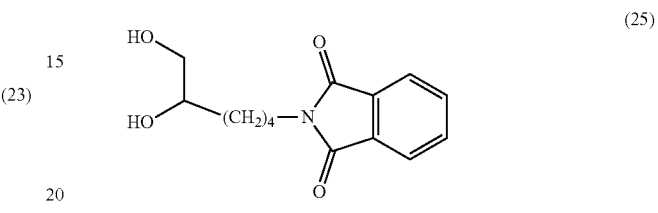

(25)

Example 5

Into a 300 mL three-necked flask equipped with a thermometer, a nitrogen inlet tube, a stirrer, a Dean-stark tube and a condenser tube were charged the compound of formula (25) (3.87 g, 14.7 mmol), 4-hydroxybenzaldehyde (1.20 g, 9.83 mmol), pyridinium p-toluenesulfonate (247 mg, 0.983 mmol) and toluene (180 g), and the reaction was performed for 4 hours while removing by-produced water by azeotropic distillation with toluene. Triethylamine (199 mg, 1.97 mmol) was added thereto and after stirring for a while, the solvent was distilled off under a reduced pressure. The residue was dissolved in chloroform, the solution was washed in order with an aqueous 20% by weight sodium chloride solution and ion-exchanged water, and the organic layer was dried over anhydrous sodium sulfate. After filtration, the solvent was distilled off under a reduced pressure to obtain a compound of formula (26).

$^1$H-NMR (CDCl$_3$, internal standard TMS); δ (ppm):
1.41-1.80 (6H, m, >CHC$\underline{H}_2$C$\underline{H}_2$C$\underline{H}_2$—), 3.57-4.26 (5H, m, —OC$\underline{H}_2$CH<, —C$\underline{H}_2$-phthalimide), 5.71 (0.6H, s, >C$\underline{H}$—), 5.82 (0.4H, s, >C$\underline{H}$—), 6.79-6.82 (2H, m, arom. $\underline{H}$), 7.31-7.35 (2H, m, arom. $\underline{H}$), 7.70-7.86 (4H, m, -phthalimide)

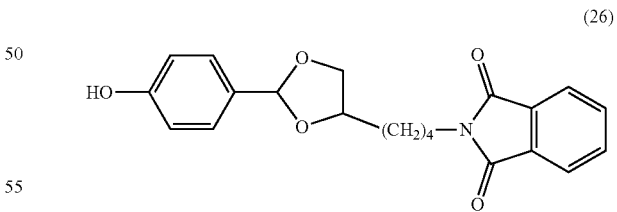

(26)

Example 6

Into a 300 mL four-necked flask equipped with a thermometer, a nitrogen inlet tube, a stirrer and a condenser tube were charged dehydrated methanol (12.8 g, 0.400 mol), dehydrated toluene (150 g) and metal sodium (0.3 g, 13 mmol), and the mixture was stirred at room temperature until the metal sodium was dissolved while bubbling nitrogen through the mixture. The solution was charged into a 5

L autoclave and after the inside of the system was substituted with nitrogen, temperature was raised to 100° C. After adding ethylene oxide (1,987 g, 45 mol) at 100 to 130° C. under a pressure of 1 MPa or less, the reaction was further continued for 2 hours. After the unreacted ethylene oxide gas was removed under a reduced pressure, the mixture was cooled to 60° C. and pH was adjusted to 7.5 with an aqueous 85% phosphoric acid solution to obtain a compound of formula (27).

$^1$H-NMR (CDCl$_3$, internal standard TMS); δ (ppm):
2.68 (1H, t, O$\underline{H}$), 3.38 (3H, s, C$\underline{H}_3$O—), 3.49-3.85 (450H, m, —(OC$\underline{H}_2$C$\underline{H}_2$)$_n$—) GPC analysis; number average molecular weight (Mn): 5119, weight average molecular weight (Mw): 5226, polydispersity (Mw/Mn): 1.021

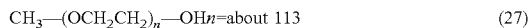

CH$_3$—(OCH$_2$CH$_2$)$_n$—OH n=about 113                (27)

Example 7

Into a 500 mL three-necked flask equipped with a thermometer, a nitrogen inlet tube, a stirrer, a Dean-stark tube and a condenser tube were charged the compound of formula (27) (100 g, 20.0 mmol) and toluene (250 g), and water was removed by azeotropic distillation with toluene. After cooling to 40° C., triethylamine (3.24 g, 32.0 mmol) was charged and methanesulfonyl chloride (2.75 g, 24.0 mmol) prepared in a dropping funnel was gradually added dropwise thereto. After the completion of the dropwise addition, the reaction was performed at 40° C. for 3 hours. Ethanol (1.11 g, 24.0 mmol) was added thereto and the mixture was stirred for a while, filtered, and diluted with ethyl acetate (200 g). Crystallization was performed by adding hexane (500 g), and after filtration, the crystals were dissolved in ethyl acetate (500 g). Crystallization was again performed by adding hexane (500 g), and after filtration, the crystals were dried under a reduced pressure to obtain a compound of formula (28).

$^1$H-NMR (CDCl$_3$, internal standard TMS); δ (ppm):
3.08 (3H, s, —OSO$_2$C$\underline{H}_3$), 3.38 (3H, s, C$\underline{H}_3$O—), 3.52-3.85 (448H, m, —(OC$\underline{H}_2$C$\underline{H}_2$)$_n$—OC$\underline{H}_2$—), 4.37-4.39 (2H, m, —C$\underline{H}_2$OSO$_2$CH$_3$)

GPC analysis; number average molecular weight (Mn): 5197, weight average molecular weight (Mw): 5306, polydispersity (Mw/Mn): 1.021

(28)

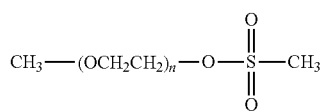

n = about 113

Example 8

Into a 100 mL three-necked flask equipped with a thermometer, a nitrogen inlet tube, a stirrer and a condenser tube were charged the compound of formula (28) (5.00 g, 1.00 mmol), the compound of formula (26) (551 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (29).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 3.38 (3H, s, C$\underline{H}_3$O—), 3.52-4.25 (455H, m, —(OC$\underline{H}_2$C$\underline{H}_2$)$_n$—, —OC$\underline{H}_2$C$\underline{H}$<, —C$\underline{H}_2$-phthalimide), 5.72 (0.6H, s, >C$\underline{H}$—), 5.84 (0.4H, s, >C$\underline{H}$—), 6.89-6.91 (2H, m, arom. $\underline{H}$), 7.35-7.39 (2H, m, arom. $\underline{H}$), 7.70-7.86 (4H, m, -phthalimide)

GPC analysis; number average molecular weight (Mn): 5462, weight average molecular weight (Mw): 5582, polydispersity (Mw/Mn): 1.022

(29)

n = about 113

Example 9

Into a 50 mL three-necked flask equipped with a thermometer, a nitrogen inlet tube, a stirrer and a condenser tube were charged the compound of formula (29) (2.00 g, 0.400 mmol), methanol (7 g) and ethylene diamine monohydrate (0.781 g, 10.0 mmol), and the reaction was performed at 40° C. for 4 hours. The mixture was diluted with an aqueous 20% by weight sodium chloride solution, extracted with dichloromethane, and the solvent was distilled off under a reduced pressure. The residue was dissolved in ethyl acetate (50 g), dried over anhydrous sodium sulfate, filtered, and crystallized by adding hexane (50 g). After filtration, the crystals were dried under a reduced pressure to obtain a compound of formula (30).

$^1$H-NMR (CD$_3$OD, internal standard TMS); δ (ppm):
1.43-1.79 (6H, m, >CHC$\underline{H}_2$C$\underline{H}_2$C$\underline{H}_2$—), 2.77 (2H, t, —C$\underline{H}_2$—NH$_2$), 3.36 (3H, s, C$\underline{H}_3$O—), 3.50-4.29 (453H, m, —(OC$\underline{H}_2$C$\underline{H}_2$)$_n$—, —OC$\underline{H}_2$C$\underline{H}$<), 5.70 (0.6H, s, >C$\underline{H}$—), 5.81 (0.4H, s, >C$\underline{H}$—), 6.93-6.98 (2H, m, arom. $\underline{H}$), 7.33-7.41 (2H, m, arom. $\underline{H}$)

GPC analysis; number average molecular weight (Mn): 5332, weight average molecular weight (Mw): 5454, polydispersity (Mw/Mn): 1.023

(30)

n = about 113

Example 10

Into a 50 mL three-necked flask equipped with a thermometer, a nitrogen inlet tube, a stirrer and a condenser tube were charged the compound of formula (30) (0.20 g, 0.040 mmol) and acetonitrile (10 g), and N-succinimidyl 3-maleimidopropionate (32 mg, 0.048 mmol) was added thereto, and the reaction was performed at 25° C. for 3 hours. After filtration, the solvent was distilled off under a reduced pressure. The residue was dissolved in ethyl acetate (25 g), and crystallized by adding hexane (25 g). After filtration, the crystals were dried under a reduced pressure to obtain a compound of formula (31).

¹H-NMR (CDCl₃, internal standard TMS); δ (ppm):
1.40-1.81 (6H, m, >CHC<u>H</u>₂C<u>H</u>₂C<u>H</u>₂—), 2.44 (2H, t, —C<u>H</u>₂CH₂-maleimide), 3.27-3.37 (2H, m, —C<u>H</u>₂NHCO—), 3.38 (3H, s, C<u>H</u>₃O—), 3.47-4.25 (455H, m, —(OC<u>H</u>₂C<u>H</u>₂)ₙ—, —OC<u>H</u>₂CH<, —CH₂C<u>H</u>₂-maleimide), 5.72 (0.6H, s, >C<u>H</u>—), 5.84 (0.4H, s, >C<u>H</u>—), 6.15 (1H, brs, —N<u>H</u>CO—), 6.70 (2H, s, -maleimide), 6.89-6.91 (2H, m, arom. <u>H</u>), 7.35-7.39 (2H, m, arom. <u>H</u>)

GPC analysis; number average molecular weight (Mn): 5484, weight average molecular weight
(Mw): 5610, polydispersity (Mw/Mn): 1.023

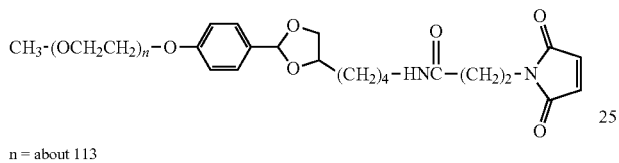

(31)

n = about 113

Example 11

A compound of formula (32) was obtained in the same manner as in Examples 1 to 8 using 3-fluoro-4-hydroxybenzaldehyde.

¹H-NMR (CDCl₃, internal standard TMS); δ (ppm):
1.38-1.80 (6H, m, >CHC<u>H</u>₂C<u>H</u>₂C<u>H</u>₂—), 3.38 (3H, s, C<u>H</u>₃O—), 3.52-4.23 (455H, m, —(OC<u>H</u>₂C<u>H</u>₂)ₙ—, —OC<u>H</u>₂C<u>H</u><, —CH₂-phthalimide), 5.70 (0.6H, s, >C<u>H</u>—), 5.82 (0.4H, s, >C<u>H</u>—), 6.95-7.21 (3H, m, arom. H), 7.70-7.86 (4H, m, -phthalimide)

GPC analysis; number average molecular weight (Mn): 5485, weight average molecular weight
(Mw): 5606, polydispersity (Mw/Mn): 1.022

(32)

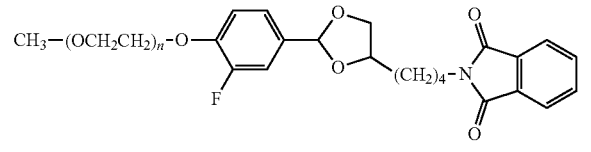

n = about 113

Example 12

A compound of formula (33) was obtained in the same manner as in Examples 1 to 8 using 2-bromo-5-hydroxybenzaldehyde.

¹H-NMR (CDCl₃, internal standard TMS); δ (ppm):
1.38-1.80 (6H, m, >CHC<u>H</u>₂C<u>H</u>₂C<u>H</u>₂—), 3.38 (3H, s, C<u>H</u>₃O—), 3.52-4.23 (455H, m, —(OC<u>H</u>₂C<u>H</u>₂)ₙ—, —OC<u>H</u>₂C<u>H</u><, —CH₂-phthalimide), 5.70 (0.6H, s, >C<u>H</u>—), 5.82 (0.4H, s, >C<u>H</u>—), 6.95-7.21 (3H, m, arom. <u>HH</u>), 7.70-7.86 (4H, m, -phthalimide)

GPC analysis; number average molecular weight (Mn): 5548, weight average molecular weight
(Mw): 5670, polydispersity (Mw/Mn): 1.022

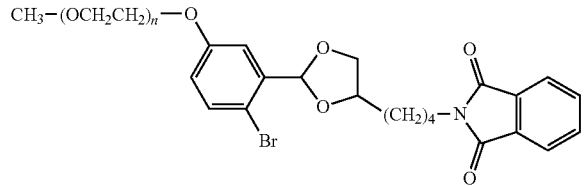

(33)

n = about 113

Example 13

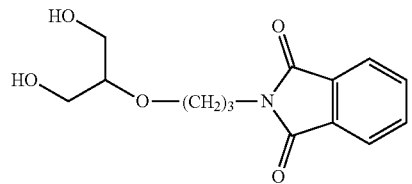

(34)

A compound of formula (34) was synthesized in a manner similar to Examples 1 to 4, and a compound of formula (35) was obtained in the same manner as in Examples 5 to 8 using 3-fluoro-4-hydroxybenzaldehyde.

¹H-NMR (CDCl₃, internal standard TMS); δ (ppm):
1.89 (2H, m, —C<u>H</u>₂CH₂-phthalimide), 3.19 (1H, m, —OCH₂C<u>H</u><), 3.38 (3H, s, C<u>H</u>₃O—), 3.52-4.41 (456H, m, —(OC<u>H</u>₂C<u>H</u>₂)ₙ—, —OC<u>H</u>₂CH<, —CH₂ CH₂C<u>H</u>₂-phthalimide), 5.34 (0.8H, s, >C<u>H</u>—), 5.42 (0.2H, s, >C<u>H</u>—), 6.95-7.25 (3H, m, arom. <u>H</u>), 7.70-7.86 (4H, m, -phthalimide)

GPC analysis; number average molecular weight (Mn): 5498, weight average molecular weight
(Mw): 5619, polydispersity (Mw/Mn): 1.022

(35)

n = about 113

Example 14

A compound of formula (36) was obtained in the same manner as in Examples 5 to 8 using the compound of formula (34) and 2-bromo-5-hydroxybenzaldehyde.

¹H-NMR (CDCl₃, internal standard TMS); δ (ppm):
1.89 (2H, m, —C<u>H</u>₂CH₂-phthalimide), 3.19 (1H, m, —OCH₂C<u>H</u><), 3.38 (3H, s, C<u>H</u>₃O—), 3.52-4.41 (456H, m, —(OCH$_2$CH$_2$)$_n$—, —OCH$_2$CH<, —CH$_2$CH$_2$CH$_2$-phthalimide), 5.61 (0.8H, s, >CH—), 5.68 (0.2H, s, >CH—), 6.78-7.40 (3H, m, arom. H), 7.70-7.86 (4H, m, -phthalimide)

GPC analysis; number average molecular weight (Mn): 5564, weight average molecular weight (Mw): 5686, polydispersity (Mw/Mn): 1.022

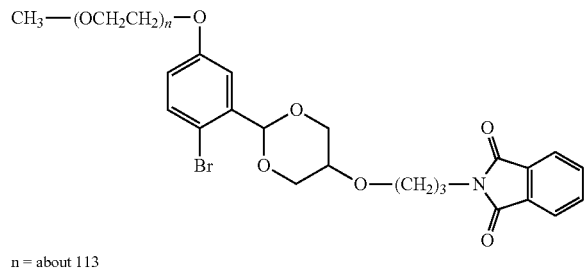

(36)

Example 15

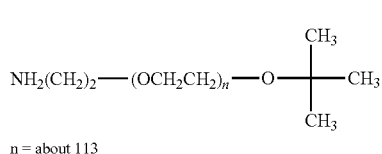

(37)

A compound of formula (38) was obtained by removing the tert-butyl group using hydrochloric acid from the compound of formula (37) synthesized according to the method described in JP-A-2010-248504.

$^1$H-NMR (D$_2$O, internal standard TMS); δ (ppm):
3.14 (2H, t, NH$_2$CH$_2$—), 3.40-4.00 (452H, n, —(OCH$_2$CH$_2$)$_n$—OCH$_2$—)

NH$_2$(CH$_2$)$_2$—(OCH$_2$CH$_2$)$_n$—OH n=about 113 (38)

Example 16

A compound of formula (39) was obtained by allowing to react the compound of formula (38) with 5-azidopentanoic anhydride.

$^1$H-NMR (CDCl$_3$, internal standard TMS); δ (ppm):
1.60-1.74 (4H, n, —CH$_2$CH$_2$CH$_2$CH$_2$N$_3$), 2.18 (2H, t, —CH$_2$CH$_2$CH$_2$CH$_2$N$_3$), 3.29 (2H, t, —CH$_2$CH$_2$CH$_2$CH$_2$N$_3$), 3.40-3.85 (454H, n, —(OCH$_2$CH$_2$)$_n$—OCH$_2$—, —CONHCH$_2$—), 6.30 (1H, brs, —CONHH—)

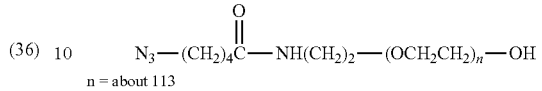

(39)

Example 17

A compound of formula (40) was obtained by allowing to react the compound of formula (39) with methanesulfonyl chloride in toluene in the presence of triethylamine in a manner similar to Example 7.

$^1$H-NMR (CDCl$_3$, internal standard TMS); δ (ppm):
1.60-1.74 (4H, m, —CH$_2$CH$_2$CH$_2$CH$_2$N$_3$), 2.18 (2H, t, —CH$_2$CH$_2$CH$_2$CH$_2$N$_3$), 3.08 (3H, s, —OSO$_2$CH$_3$), 3.29 (2H, t, —CH$_2$CH$_2$CH$_2$CH$_2$N$_3$), 3.40-3.85 (452H, m, —(OCH$_2$CH$_2$)$_n$—OCH$_2$—, —CONHCH$_2$—), 4.37-4.39 (2H, m, —CH$_2$OSO$_2$CH$_3$), 6.30 (1H, brs, —CH$_2$CONH—)

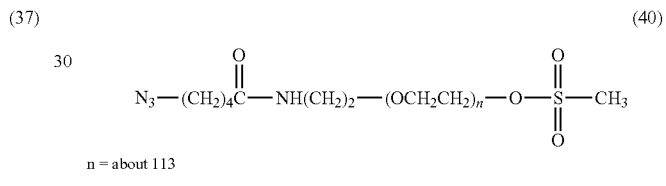

(40)

Example 18

A compound of formula (41) was obtained using 3-fluoro-4-hydroxybenzaldehyde and the compound of formula (40) in the same manner as in Examples 1 to 5 and 8.

$^1$H-NMR (CDCl$_3$, internal standard TMS); δ (ppm):
1.38-1.80 (10H, m, >CHCH$_2$CH$_2$CH$_2$—, —CH$_2$CH$_2$CH$_2$CH$_2$N$_3$), 2.18 (2H, t, —CH$_2$CH$_2$CH$_2$CH$_2$N$_3$), 3.28-4.23 (461H, m, —(OCH$_2$CH$_2$)$_n$—OCH$_2$—, —CH$_2$CH$_2$CH$_2$CH$_2$N$_3$, —CH$_2$CONHCH$_2$—, —OCH$_2$CH<, —CH$_2$-phthalimide), 5.70 (0.6H, s, >CH—), 5.82 (0.4H, s, >CH—), 6.30 (1H, brs, —CH$_2$CONH—), 6.95-7.21 (3H, m, arom. H), 7.70-7.86 (4H, m, -phthalimide)

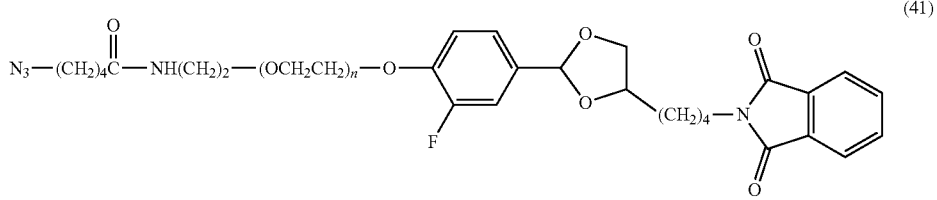

(41)

Example 19

A compound of formula (42) was obtained by deprotection of the phthalimide group from the compound of formula (41) in the same manner as in Example 9, followed by allowing to react with iodoacetic anhydride.

$^1$H-NMR (CDCl$_3$, internal standard TMS); δ (ppm):
1.38-1.80 (10H, m, >CHC$\underline{H}_2$C$\underline{H}_2$C$\underline{H}_2$—, —CH$_2$CH$_2$C$\underline{H}_2$CH$_2$N$_3$), 2.18 (2H, t, —C$\underline{H}_2$CH$_2$CH$_2$CH$_2$N$_3$), 3.28-4.23 (463H, m, —(OC$\underline{H}_2$C$\underline{H}_2$)$_n$—OC$\underline{H}_2$—, —CH$_2$CH$_2$CH$_2$C$\underline{H}_2$N$_3$, —CH$_2$CONHC$\underline{H}_2$—, ICH$_2$CONHC$\underline{H}\underline{H}_2$—, IC$\underline{H}\underline{H}_2$CONHCH$_2$—, —OC$\underline{H}_2$CH<), 5.70 (0.6H, s, >C$\underline{H}$—), 5.82 (0.4H, s, >C$\underline{H}$—), 6.30 (1H, brs, —CH$_2$CON$\underline{H}$—), 6.96 (1H, brs, ICH$_2$CON$\underline{H}$CH$_2$—), 6.95-7.21 (3H, m, arom. $\underline{H}$)

GPC analysis; number average molecular weight (Mn): 5679, weight average molecular weight
(Mw): 5815, polydispersity (Mw/Mn): 1.024

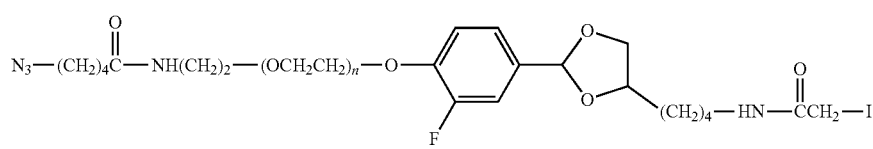

(42)

n = about 113

Example 20

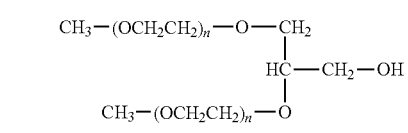

(43)

n = about 113

A compound of formula (44) was obtained by allowing to react the compound of formula (43) synthesized according to the method described in JP-A-2004-197077 with methanesulfonyl chloride in the same manner as in Example 7.

$^1$H-NMR (CDCl$_3$, internal standard TMS); δ (ppm):
3.08 (3H, s, —OSO$_2$C$\underline{H}_3$), 3.38 (6H, s, C$\underline{H}_3$O—), 3.40-4.00 (903H, m, —(OC$\underline{H}_2$C$\underline{H}_2$)$_n$—OC$\underline{H}_2$—, —(OCH$_2$C$\underline{H}_2$)$_n$—OC$\underline{H}$<), 4.26-4.42 (2H, m, —C$\underline{H}_2$OSO$_2$CH$_3$)

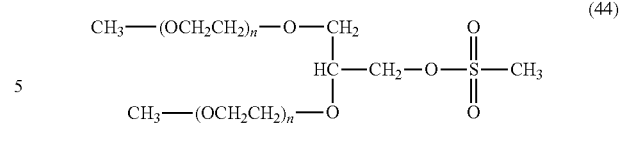

(44)

n = about 113

Example 21

A compound of formula (45) was obtained using 3-fluoro-4-hydroxybenzaldehyde and the compound of formula (44) in the same manner as in Examples 1 to 5 and 8.

$^1$H-NMR (CDCl$_3$, internal standard TMS); δ (ppm):
1.38-1.80 (6H, m, >CHC$\underline{H}_2$C$\underline{H}_2$C$\underline{H}_2$—), 3.38 (6H, s, C$\underline{H}_3$O—), 3.40-4.23 (910H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —OC$\underline{H}_2$CH<, —C$\underline{H}_2$-phthalimide), 5.70 (0.6H, s, >C$\underline{H}$H—), 5.82 (0.4H, s, >C$\underline{H}$—), 6.95-7.21 (3H, m, arom. $\underline{H}$), 7.70-7.86 (4H, m, -phthalimide)

GPC analysis; number average molecular weight (Mn): 9761, weight average molecular weight
(Mw): 9986, polydispersity (Mw/Mn): 1.023

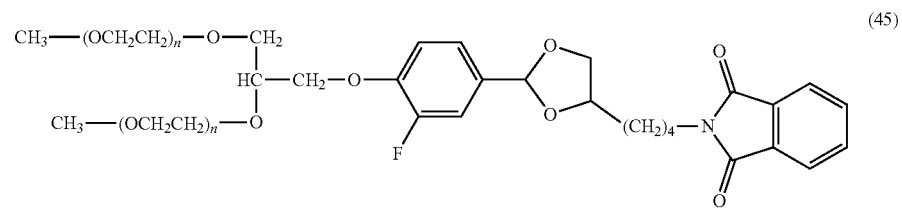

(45)

n = about 113

Example 22

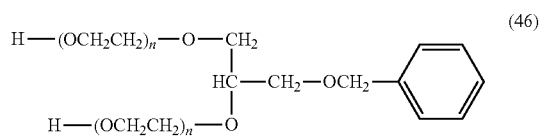

(46)

n = about 113

A compound of formula (47) was obtained by allowing to react the compound of formula (46) synthesized according to the method described in JP-A-2004-197077 with acetic anhydride in the presence of triethylamine and 4-dimethylaminopyridine.

$^1$H-NMR (CDCl$_3$, internal standard TMS); δ (ppm):
2.08 (6H, s, C$\underline{H}_3$CO—), 3.40-4.00 (901H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —C$\underline{H}_2$OCH$_2$Ph), 4.22 (4H, t, CH$_3$CO$_2$C$\underline{H}_2$—), 4.54 (2H, s, —CH$_2$OC$\underline{H}_2$Ph), 7.27-7.38 (5H, m, —CH$_2$OCH$_2$P$\underline{h}$)

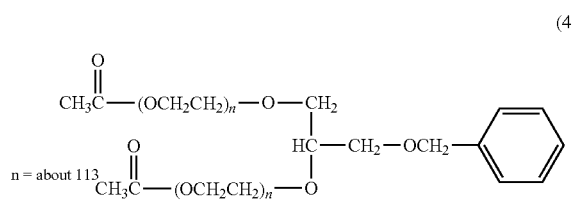

(47)

n = about 113

Example 23

A compound of formula (48) was obtained by removing the benzyl group from the compound of formula (47) according to the method described in JP-A-2004-197077, followed by allowing to react with methanesulfonyl chloride in a manner similar to Example 7.

$^1$H-NMR (CDCl$_3$, internal standard TMS); δ (ppm):
2.08 (6H, s, C$\underline{H}_3$CO—), 3.08 (3H, s, —OSO$_2$C$\underline{H}_3$), 3.40-4.00 (899H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<), 4.22 (4H, t, CH$_3$CO$_2$C$\underline{H}_2$—), 4.26-4.42 (2H, m, —C$\underline{H}_2$OSO$_2$CH$_3$)

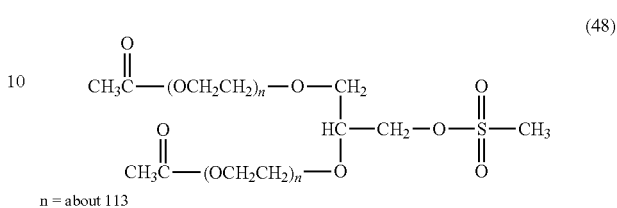

(48)

n = about 113

Example 24

A compound of formula (49) was obtained using 3-fluoro-4-hydroxybenzaldehyde and the compound of formula (48) in the same manner as in Examples 1 to 5 and 8.

$^1$H-NMR (CDCl$_3$, internal standard TMS); δ (ppm):
1.38-1.80 (6H, m, >CHC$\underline{H}_2$C$\underline{H}_2$C$\underline{H}_2$—), 2.08 (6H, s, C$\underline{H}_3$CO—), 3.40-4.23 (910H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —OC$\underline{H}_2$C$\underline{H}$<, —C$\underline{H}_2$-phthalimide, CH$_3$CO$_2$C$\underline{H}_2$—), 5.70 (0.6H, s, >C$\underline{H}$—), 5.82 (0.4H, s, >C$\underline{H}$—), 6.95-7.21 (3H, m, arom. $\underline{H}$), 7.70-7.86 (4H, m, -phthalimide)

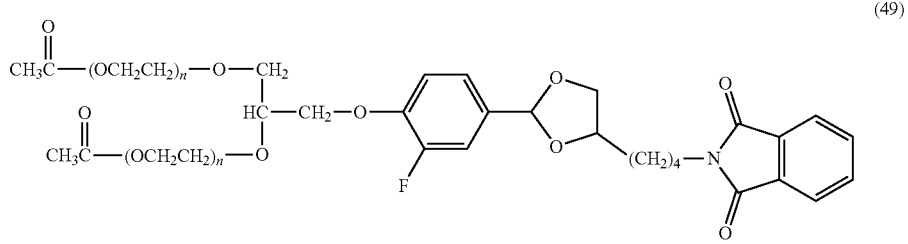

(49)

n = about 113

Example 25

A compound of formula (50) was obtained by deprotection of the phthalimide group using ethylene diamine monohydrate and the removal of the acetyl group using an aqueous sodium hydroxide solution from the compound of formula (49), followed by allowing to react with N-succinimidyl 3-maleimidopropionate in the same manner as in Example 10.

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.44 (2H, t, —C$\underline{H}_2$CH$_2$-maleimide), 3.27-3.37 (2H, m, —C$\underline{H}_2$NHCO—), 3.40-4.23 (910H, m, —(OC$\underline{H}_2$C$\underline{H}_2$)$_n$—OC$\underline{H}_2$—, —(OC$\underline{H}_2$C$\underline{H}_2$)$_n$—OC$\underline{H}$<, —OC$\underline{H}_2$C$\underline{H}$<, —CH$_2$C$\underline{H}_2$-maleimide), 5.70 (0.6H, s, >C$\underline{H}$—), 5.82 (0.4H, s, >C$\underline{H}$—), 6.15 (1H, brs, —N$\underline{H}$CO—), 6.70 (2H, s, -maleimide), 6.95-7.21 (3H, m, arom. $\underline{H}$)

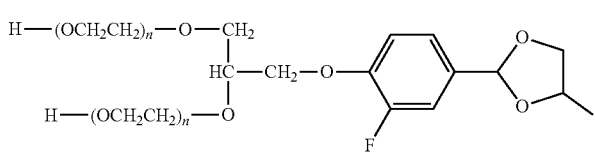
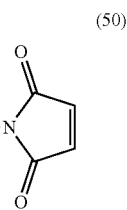

(50)

n = about 113

Example 26

A compound of formula (51) was obtained by allowing to react the compound of formula (50) with N,N'-disuccinimidyl carbonate in dichloromethane in the presence of triethylamine.

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.44 (2H, t, —C$\underline{H}_2$CH$_2$-maleimide), 2.84 (8H, s, -succinimide), 3.27-3.37 (2H, m, —C$\underline{H}_2$NHCO—), 3.40-4.23 (906H, m, —(OCH$_2$C$\underline{H}_2$)$_n$—OC$\underline{H}_2$—, —(OC$\underline{H}_2$CH$_2$)$_n$—OC$\underline{H}$<, —OC$\underline{H}_2$C$\underline{H}$<, —CH$_2$C$\underline{H}_2$-maleimide), 4.44-4.48 (4H, m, —C$\underline{H}_2$O—COO-succinimide), 5.70 (0.6H, s, >C$\underline{H}$—), 5.82 (0.4H, s, >C$\underline{H}$—), 6.15 (1H, brs, —N$\underline{H}$CO—), 6.70 (2H, s, -maleimide), 6.95-7.21 (3H, m, arom. $\underline{H}$)

GPC analysis; number average molecular weight (Mn): 9955, weight average molecular weight (Mw): 10204, polydispersity (Mw/Mn): 1.025

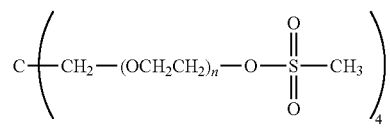

(53)

n = about 113

Example 27

A compound of formula (54) was obtained using 3-fluoro-4-hydroxybenzaldehyde and the compound of formula (53) in the same manner as in Examples 1 to 5 and 8.

$^1$H-NMR (CDCl$_3$, internal standard TMS); δ (ppm):
1.38-1.80 (24H, m, >CHC$\underline{H}_2$C$\underline{H}_2$C$\underline{H}_2$—), 3.52-4.23 (1828H, m, —(OC$\underline{H}_2$CH$_2$)$_n$—OC$\underline{H}_2$—, —OC$\underline{H}_2$CH<, —C

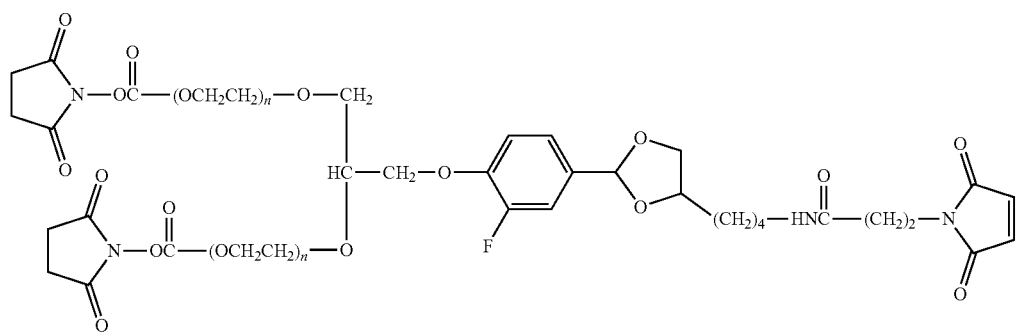

(51)

n = about 113

Example 27

(52)

n = about 113

A compound of formula (53) was obtained by allowing to react a compound of formula (52) synthesized by polymerizing ethylene oxide to pentaerythritol with methanesulfonyl chloride in the same manner as in Example 7.

$^1$H-NMR (CDCl$_3$, internal standard TMS); δ (ppm):
3.08 (12H, s, —OSO$_2$C$\underline{H}_3$), 3.47-3.85 (1800H, m, —(OC$\underline{H}_2$CH$_2$)$_n$—OC$\underline{H}_2$—), 4.37-4.39 (8H, m, —C$\underline{H}_2$OSO$_2$CH$_3$)

$\underline{H}_2$-phthalimide), 5.70 (2.4H, s, >C$\underline{H}$—), 5.82 (1.6H, s, >C$\underline{H}$—), 6.95-7.21 (12H, m, arom. $\underline{H}$), 7.70-7.86 (16H, m, -phthalimide)

GPC analysis; number average molecular weight (Mn): 19645, weight average molecular weight (Mw): 20136, polydispersity (Mw/Mn): 1.025

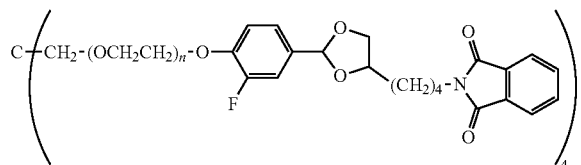

(54)

n = about 113

Example 28

Figure 2:
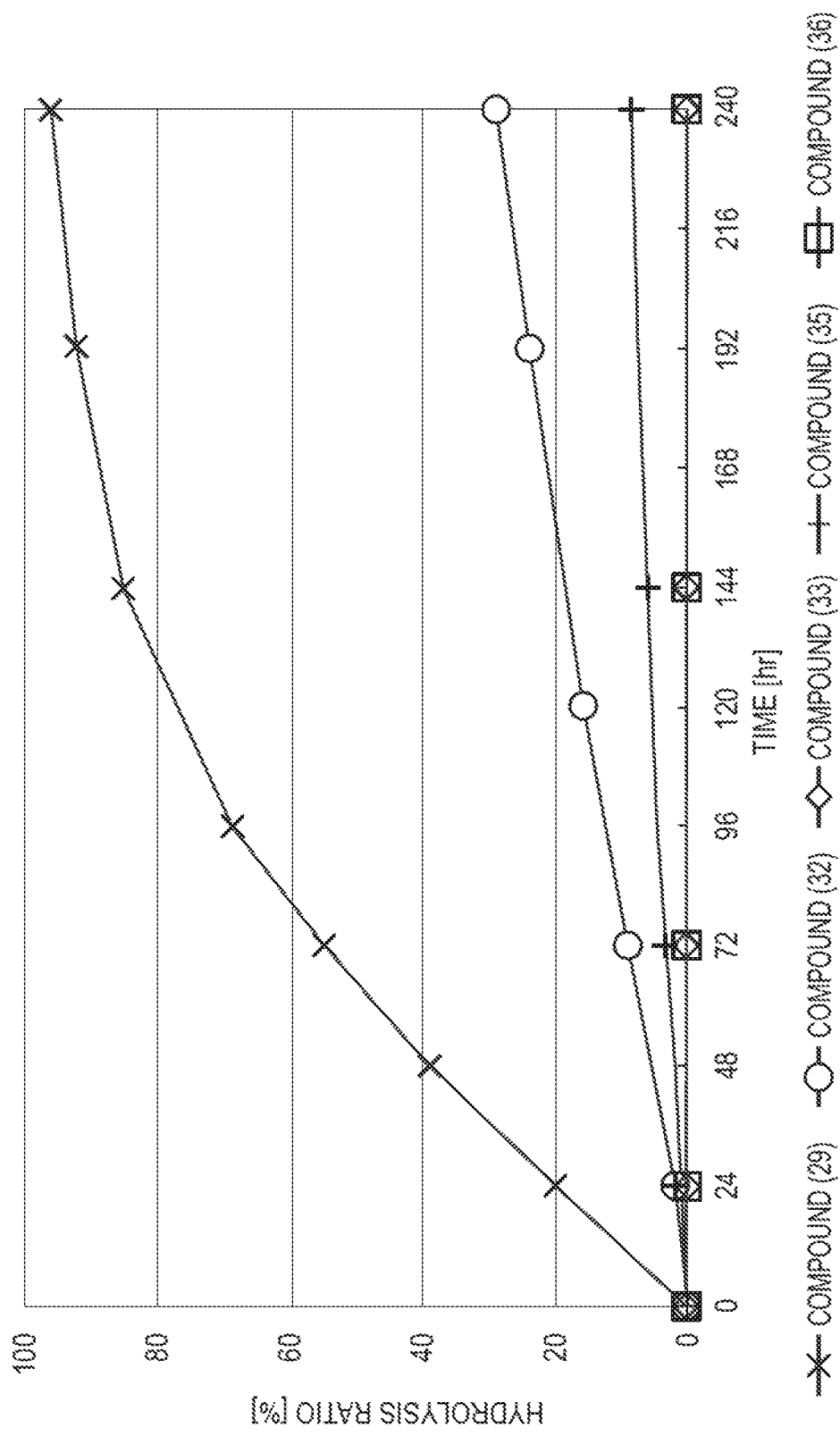
FIG. 2 shows results of the hydrolysis test in HEPES deuterated water buffer at pD 7.4 at 37° C. using the compounds of formula (29), formula (32), formula (33), formula (35) and formula (36) described in Examples.

Each of the compounds (20 mg) of formula (29), formula (32), formula (33), formula (35) and formula (36) was dissolved in MES deuterated water buffer (1 mL) of pD 5.5 and in HEPES deuterated water buffer (1 mL) of pD 7.4, and allowed to stand in a thermostatic bath at 37° C. FIG. 1 and FIG. 2 show the measurement results of hydrolysis rates at pD 5.5 and pD 7.4, respectively.

As shown in FIG. 1, the hydrolysis rate half-lives ($t_{1/2}$) of the compounds of formula (29), formula (32), formula (33), formula (35) and formula (36) at pD 5.5 and 37° C. were 2 hours, 12 hours, 30 days, 24 hours and 6 months, respectively. Further, as shown in FIG. 2, at pD 7.4 and 37° C., the hydrolysis rate half-lives ($t_{1/2}$) of the compounds of formula (29) and formula (32) were 65 hours and 18 days, respectively, the hydrolysis of approximately 17% was observed for 18 days for the compound of formula (35), and no hydrolysis was observed even after 18 days for the compounds of formula (33) and the formula (36).

Example 29

Into a 100 mL three-necked flask equipped with a thermometer, a nitrogen inlet tube, a stirrer and a condenser tube were charged the compound of formula (26) (1.10 g, 3.00 mmol), methanol (53 g) and ethylenediamine monohydrate (5.86 g, 75.0 mmol), and the reaction was performed at 40° C. for 4 hours. The mixture was cooled to room temperature, diluted with an aqueous 10% by weight sodium chloride solution, and extracted with dichloromethane. The organic layer was washed with an aqueous 10% by weight sodium chloride solution, and dried over anhydrous sodium sulfate. After filtration, the solvent was distilled off under a reduced pressure to obtain a compound of formula (56).

$^1$H-NMR (CD$_3$OD, internal standard TMS); δ (ppm):
1.44-1.80 (6H, m, >CHC$\underline{H}_2$C$\underline{H}_2$C$\underline{H}_2$—), 2.77 (2H, t, —C$\underline{H}_2$—NH$_2$), 3.55-4.31 (3H, m, —OC$\underline{H}_2$C$\underline{H}$<), 5.70 (0.6H, s, >C$\underline{H}$—), 5.81 (0.4H, s, >C$\underline{H}$—), 6.89-6.94 (2H, m, arom. $\underline{H}$), 7.29-7.37 (2H, m, arom. $\underline{H}$)

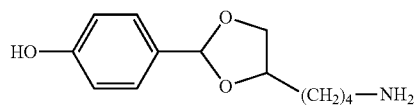

(56)

Example 30

Into a 100 mL three-necked flask equipped with a thermometer, a nitrogen inlet tube and a stirrer were charged the compound of formula (56) (593 mg, 2.50 mmol) and dehydrated methanol (20 g) and the mixture was stirred while adding dropwise a solution obtained by dissolving ethyl trifluoroacetate (426 mg, 3.00 mmol) in dehydrated methanol (20 g). After the completion of the dropwise addition, the reaction was performed at 25° C. for 2 hours. The solvent was distilled off under a reduced pressure, and the residue was dried under a reduced pressure to obtain a compound of formula (57).

$^1$H-NMR (CDCl$_3$, internal standard TMS); δ (ppm):
1.44-1.80 (6H, m, >CHC$\underline{H}_2$C$\underline{H}_2$C$\underline{H}_2$—), 3.57-4.26 (5H, m, —OC$\underline{H}_2$C$\underline{H}$<, —C$\underline{H}_2$—NHCOCF$_3$), 5.71 (0.6H, s, >C$\underline{H}$—), 5.82 (0.4H, s, >C$\underline{H}$—), 6.79-6.82 (2H, m, arom. $\underline{H}$), 7.31-7.35 (3H, m, arom. $\underline{H}$, —N$\underline{H}$COCF$_3$)

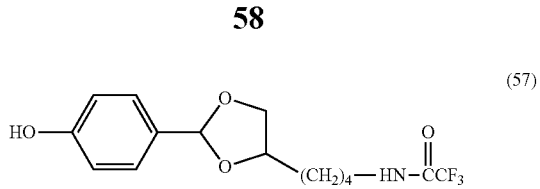

(57)

Example 31

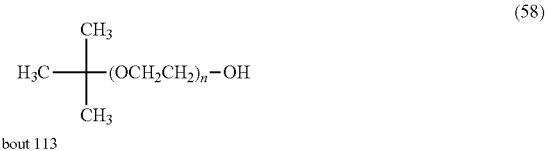

(58)

n = about 113

A compound of formula (59) was obtained by allowing to react the compound of formula (58) synthesized according to the method described in JP-A-2010-138388 with methanesulfonyl chloride in the same manner as in Example 7, followed by removing the tert-butyl group using hydrochloric acid.

$^1$H-NMR (CDCl$_3$, internal standard TMS); δ (ppm):
2.68 (1H, t, —O$\underline{H}$), 3.08 (3H, s, —OSO$_2$C$\underline{H}_3$), 3.52-3.85 (448H, m, —(OC$\underline{H}_2$C$\underline{H}_2$)$_n$—OC$\underline{H}_2$—), 4.37-4.39 (2H, m, —C$\underline{H}_2$OSO$_2$CH$_3$)

GPC analysis; number average molecular weight (Mn): 5195, weight average molecular weight
(Mw): 5309, polydispersity (Mw/Mn): 1.022

Example 32

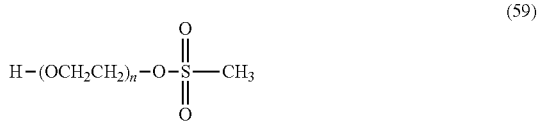

(59)

n = about 113

Into a 100 mL three-necked flask equipped with a thermometer, a nitrogen inlet tube, a stirrer and a condenser tube were charged the compound of formula (59) (5.00 g, 1.00 mmol), the compound of formula (57) (500 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g), and the solution was filtered. Crystallization was performed by adding hexane (100 g), and after filtration, the crystals were dried under a reduced pressure to obtain a compound of formula (60).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.68 (1H, t, —O$\underline{H}$), 3.52-4.25 (455H, m, —(OC$\underline{H}_2$C$\underline{H}_2$)$_n$—, —OC$\underline{H}_2$C$\underline{H}$<, —C$\underline{H}_2$—NHCOCF$_3$), 5.72 (0.6H, s, >C$\underline{H}$—), 5.84 (0.4H, s, >C$\underline{H}$—), 6.89-6.91 (2H, m, arom. $\underline{HH}$), 7.31-7.39 (3H, m, arom. $\underline{H}$, —N$\underline{H}$COCF$_3$)

GPC analysis; number average molecular weight (Mn): 5432, weight average molecular weight
(Mw): 5552, polydispersity (Mw/Mn): 1.022

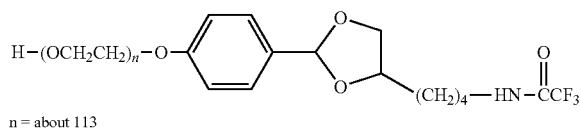

(60)

n = about 113

Example 33

Into a 100 mL three-necked flask equipped with a thermometer, a nitrogen inlet tube and a stirrer were charged the compound of formula (60) (1.00 g, 0.200 mmol) and dichloromethane (5 g), and glutaric anhydride (34.2 mg, 0,300 mmol), triethylamine (30.4 mg, 0,300 mmol) and 4-dimethylaminopyridine (1.2 mg, 0.015 mmol) were added thereto, and the reaction was performed at 25° C. for 6 hours. After filtration, the solvent was distilled off under a reduced pressure. The residue was dissolved in methanol (2.5 g), and a 1M aqueous potassium carbonate solution (5 g) was added thereto, and the reaction was performed at 25° C. for 3 hours. The mixture was diluted with an aqueous 20% by weight sodium chloride solution, extracted with dichloromethane, and the solvent was distilled off under a reduced pressure. The residue was dissolved in ethyl acetate (50 g), dried over anhydrous sodium sulfate, filtered, and crystallized by adding hexane (50 g). After filtration, the crystals were dried under a reduced pressure to obtain a compound of formula (61).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 1.97 (2H, quin, —CH$_2$C$\underline{H}_2$CH$_2$COOH), 2.38-2.46 (4H, m, —C$\underline{H}_2$CH$_2$C$\underline{H}_2$COOH), 2.71 (2H, t, —C$\underline{H}_2$—NH$_2$), 3.52-4.27 (455H, m, —(OC$\underline{H}_2$CH$_2$)$_n$—, —OC$\underline{H}_2$CH<, —C$\underline{H}_2$O—COCH$_2$—), 5.72 (0.6H, s, >C$\underline{H}$—), 5.84 (0.4H, s, >C$\underline{H}$—), 6.89-6.91 (2H, m, arom. $\underline{H}$), 7.35-7.39 (2H, m, arom. $\underline{H}$)

GPC analysis; number average molecular weight (Mn): 5449, weight average molecular weight
(Mw): 5569, polydispersity (Mw/Mn): 1.022

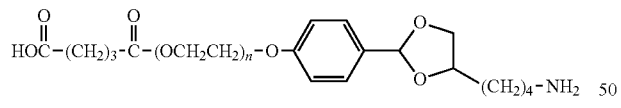

(61)

n = about 113

Example 34

Into a 300 mL three-necked flask equipped with a thermometer, a nitrogen inlet tube, a stirrer, a Dean-stark tube and a condenser tube were charged 1,2,6-hexanetriol (2.01 g, 15.0 mmol), 4-hydroxybenzaldehyde (1.22 g, 10.0 mmol), p-toluenesulfonic acid monohydrate (19.0 mg, 0.100 mmol) and toluene (183 g), and the reaction was performed for 4 hours while removing by-produced water by azeotropic distillation with toluene. Triethylamine (20.2 mg, 0.200 mmol) was added thereto and after stirring for a while, the mixture was washed with an aqueous 10% by weight sodium chloride solution, and the organic layer was dried over anhydrous sodium sulfate. After filtration, the solvent was distilled off under a reduced pressure to obtain a compound of formula (62).

$^1$H-NMR (CDCl$_3$, internal standard TMS); δ (ppm):
1.42-1.80 (6H, m, >CHC$\underline{H}_2$C$\underline{H}_2$C$\underline{H}_2$—), 3.57-4.26 (5H, m, —OC$\underline{H}_2$C$\underline{H}$<, —C$\underline{H}_2$—OH), 5.71 (0.6H, s, >C$\underline{H}$—), 5.82 (0.4H, s, >C$\underline{H}$—), 6.79-6.82 (2H, m, arom. $\underline{H}$), 7.31-7.35 (2H, m, arom. $\underline{H}$)

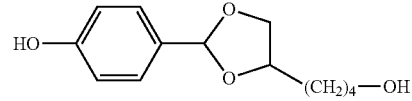

(62)

Example 35

Into a 100 mL three-necked flask equipped with a thermometer, a nitrogen inlet tube, a stirrer and a condenser tube were charged the compound of formula (28) (5.00 g, 1.00 mmol), the compound of formula (62) (357 mg, 1.50 mmol), potassium carbonate (691 mg, 5.00 mmol) and acetonitrile (25 g), and the reaction was performed at 80° C. for 4 hours. After distilled off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (63).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 3.38 (3H, s, C$\underline{H}_3$O—), 3.52-4.25 (455H, m, —(OC$\underline{H}_2$CH$_2$)$_n$—, —OC$\underline{H}_2$C$\underline{H}$<, —C$\underline{H}_2$—OH), 5.72 (0.6H, s, >C$\underline{H}$—), 5.84 (0.4H, s, >C$\underline{H}$—), 6.89-6.91 (2H, m, arom. $\underline{H}$), 7.35-7.39 (2H, m, arom. $\underline{H}$)

GPC analysis; number average molecular weight (Mn): 5332, weight average molecular weight
(Mw): 5449, polydispersity (Mw/Mn): 1.022

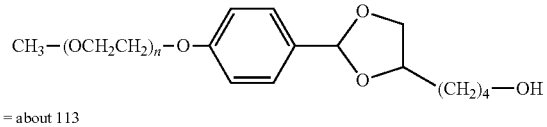

(63)

n = about 113

Example 36

A compound of formula (64) was obtained by allowing to react the compound of formula (63) with N,N'-disuccinimidyl carbonate in dichloromethane in the presence of triethylamine.

$^1$H-NMR (CDCl$_3$, internal standard TMS); δ (ppm):
1.45-1.87 (6H, m, >CHC$\underline{H}_2$C$\underline{H}_2$C$\underline{H}_2$—), 2.84 (4H, two singlets, -succinimide), 3.38 (3H, s, C$\underline{H}_3$O—), 3.52-4.38 (455H, m, —(OC$\underline{H}_2$CH$_2$)$_n$—, —OC$\underline{H}_2$C$\underline{H}$<, —C$\underline{H}_2$O—COO-succinimide), 5.72 (0.6H, s, >C$\underline{H}$—), 5.84 (0.4H, s, >C$\underline{H}$—), 6.89-6.91 (2H, m, arom. $\underline{H}$), 7.35-7.39 (2H, m, arom. $\underline{H}$)

GPC analysis; number average molecular weight (Mn): 5470, weight average molecular weight (Mw): 5590, polydispersity (Mw/Mn): 1.022

(64)

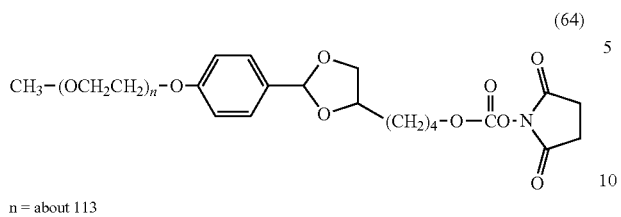

n = about 113

While the invention has been described in detail and with reference to specific embodiments thereof, it will be apparent to those skilled in the art that various changes and modifications can be made therein without departing from the spirit and scope of the invention.

This application is based on a Japanese patent application filed on Mar. 31, 2014 (Japanese Patent Application No. 2014-72356 and Japanese patent application filed on Sep. 22, 2014 (Japanese Patent Application No. 2014-193039, and the whole contents thereof are incorporated herein by reference. Also, all the references cited herein are incorporated as a whole.

The invention claimed is:

1. A method for chemical modification of a biofunctional molecule with a hydrophilic polymer compound for improving in vivo and intracellular kinetics in environments having different pH in a living body, which comprises reacting a functional group in the biofunctional molecule with a chemically reactive functional group in the hydrophilic polymer, wherein the hydrophilic polymer compound has a cyclic benzylidene acetal linker represented by formula (1):

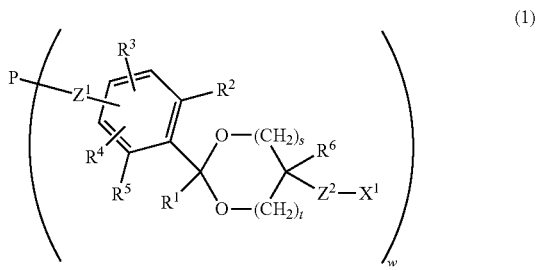

(1)

wherein $R^1$ and $R^6$ are each independently a hydrogen atom or a hydrocarbon group;
$R^2$, $R^3$, $R^4$ and $R^5$ are each independently an electron-withdrawing or electron-donating substituent or a hydrogen atom;
$X^1$ is the chemically reactive functional group and is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an a-haloacetyl group, an alkynyl group, an allyl group, a vinyl group, an amino group, an oxyamino group, a hydrazide group and an azide group;
P is a hydrophilic polymer;
s is 1 or 2, t is 0 or 1, and s+t is 1 or 2;
m is an integer of 1 to 8; and
$Z^1$ and $Z^2$ are each independently a selected divalent spacer.

2. The method as claimed in claim 1, wherein s is 1 and t is 0, and $R^2$ and $R^5$ are each a hydrogen atom,
wherein the electron-withdrawing substituent is at least one selected from the group consisting of an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and
the electron-donating substituent is at least one selected from the group consisting of an alkyl group having from 1 to 4 carbon atoms, an alkoxy group having from 1 to 4 carbon atoms, an aryl group having from 6 to 10 carbon atom and an aryloxy group having from 6 to 10 carbon atoms.

3. The method as claimed in claim 1, wherein s is 1 and t is 0, and at least one of $R^2$ and $R^5$ is an electron-withdrawing or electron-donating substituent,
wherein the electron-withdrawing substituent is at least one selected from the group consisting of an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and
the electron-donating substituent is at least one selected from the group consisting of an alkyl group having from 1 to 4 carbon atoms, an alkoxy group having from 1 to 4 carbon atoms, an aryl group having from 6 to 10 carbon atom and an aryloxy group having from 6 to 10 carbon atoms.

4. The method as claimed in claim 1, wherein s is 1 and t is 1, or s is 2 and t is 0, $R^2$ and $R^5$ are each a hydrogen atom.

5. The method as claimed in claim 1, wherein in formula (1), s is 1 and t is 1, or s is 2 and t is 0, and at least one of $R^2$ and $R^5$ is an electron-withdrawing or electron-donating substituent.

6. The method as claimed in claim 1, wherein $X^1$ is selected from the group consisting of formula (a), formula (b), formula (c), formula (d), formula (e), formula (f), formula (g), formula (h), formula (i), formula (j), formula (k), formula (1), formula (m) and formula (n):

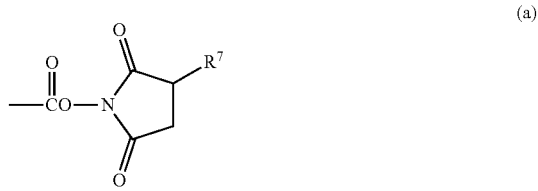

(a)

-continued

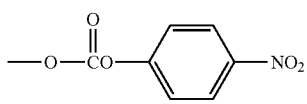 (b)

 (c)

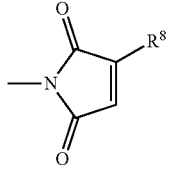 (d)

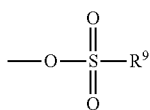 (e)

—COOH (f)

—SH (g)

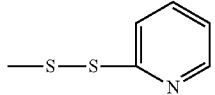 (h)

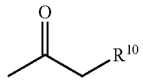 (i)

—C≡C—R<sup>11</sup> (j)

—NH<sub>2</sub> (k)

—O—NH<sub>2</sub> (l)

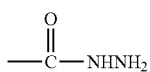 (m)

—N<sub>3</sub> (n)

wherein $R^7$ is a hydrogen atom or a sulfo group; $R^8$ and $R^{11}$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from a chlorine atom, a bromine atom and an iodine atom.

7. The method as claimed in claim 1, wherein $Z^1$ and $Z^2$ are each independently an ether bond, an ester bond, a carbonate bond, a urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

8. The method as claimed in claim 1, wherein P is a linear polyethylene glycol having a hydrocarbon group or a chemically reactive functional group at its terminal,
wherein the chemically reactive functional group is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an a-haloacetyl group, an alkynyl group, an allyl group, a vinyl group, an amino group, an oxyamino group, a hydrazide group and an azide group.

9. The method as claimed in claim 8, wherein w is 1, and P is represented by formula (2):

$$Y—(OCH_2CH_2)_n \quad (2)$$

wherein Y is a hydrocarbon group having from 1 to 24 carbon atoms; and n is an integer of 3 to 2,000.

10. The method as claimed in claim 8, wherein w is 1, and P is represented by formula (3):

$$X^2—Z^3—(OCH_2CH_2)_n \quad (3)$$

wherein $X^2$ is a chemically reactive functional group different from $X^1$; $Z^3$ is a divalent spacer; and n is an integer of 3 to 2,000.

11. The method as claimed in claim 1, wherein P is a branched polyethylene glycol having a hydrocarbon group or a chemically reactive functional group different from $X^1$ at its terminal.

12. The method as claimed in claim 11, wherein w is 1, and P is represented by formula (4):

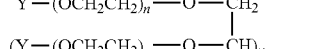
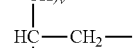
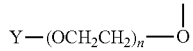

(4)

wherein Y is a hydrocarbon group having from 1 to 24 carbon atoms; n is an integer of 3 to 1,000; and v is 0 or 2.

13. The method as claimed in claim 11, wherein w is 1, and P is represented by formula (5):

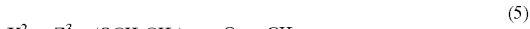
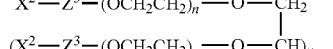
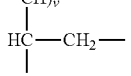

(5)

wherein $X^2$ is a chemically reactive functional group different from $X^1$; $Z^3$ is a divalent spacer; n is an integer of 3 to 1,000; and v is 0 or 2.

14. The method as claimed in claim 11, wherein w is v+2, and P is represented by formula (6):

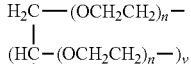
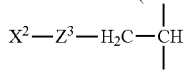

(6)

wherein $X^2$ is a chemically reactive functional group different from $X^1$; $Z^3$ is a divalent spacer; n is an integer of 3 to 1,000; and v is 0 or 2.

15. The method as claimed in claim 10, wherein $X^2$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

16. The method as claimed in claim 10, wherein $X^2$ is selected from the group consisting of formula (a), formula (b), formula (c), formula (d), formula (e), formula (0, formula (g), formula (h), formula (i), formula (j), formula (k), formula (1), formula (m) and formula (n):

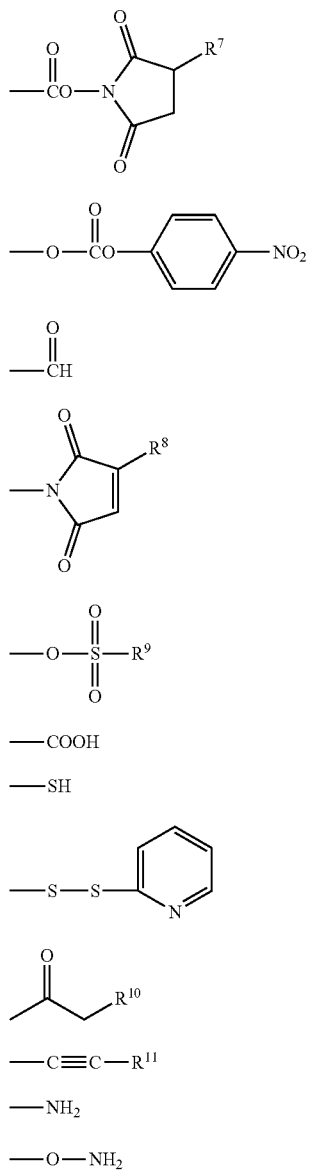

-continued

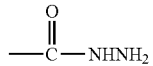

(m)

(n)

wherein $R^7$ is a hydrogen atom or a sulfo group; $R^8$ and $R^{11}$ are each independently a hydrogen atom or a hydrocarbon group having from 1 to 5 carbon atoms; $R^9$ is a hydrocarbon group having from 1 to 10 carbon atoms which may contain a halogen atom; and $R^{10}$ is a halogen atom selected from a chlorine atom, a bromine atom and an iodine atom.

17. The method as claimed in claim 10, wherein $Z^3$ is an ether bond, an ester bond, a carbonate bond, a urethane bond, an amide bond, a secondary amino group, an alkylene group containing any of these bonds and group, a single bond or an alkylene group, and in a case where $Z^3$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

18. The method as claimed in claim 1, wherein P is polyethylene glycol having a number of terminals of 2 to 8, all the terminals of the polyethylene glycol constituting P are each connected to $Z^1$, and w is equal to the number of terminals of the polyethylene glycol.

19. The method as claimed in claim 18, wherein P is selected from the group consisting of formula (r), formula (s), formula (t), formula (u) and formula (v):

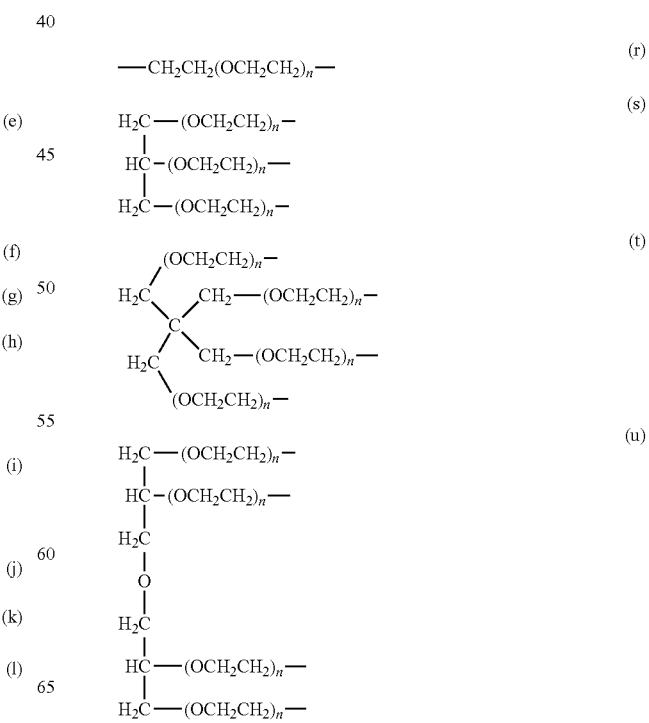

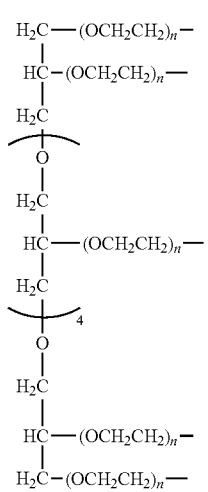
(v)
wherein n is an integer of 3 to 2,000, and w is 2 when P is represented by formula (r), w is 3 when P is represented by formula (s), w is 4 when P is represented by formula (t), w is 4 when P is represented by formula (u), and w is 8 when P is represented by formula (v).
* * * * *